(12) United States Patent
Mooney et al.

(10) Patent No.: US 11,234,888 B2
(45) Date of Patent: Feb. 1, 2022

(54) WEARABLE JOINT AUGMENTATION SYSTEM

(71) Applicant: Dephy, Inc., Maynard, MA (US)

(72) Inventors: Luke Mooney, Sudbury, MA (US); Jean-Francois Duval, Belmont, MA (US); Hugh Herr, Somerville, MA (US)

(73) Assignee: Dephy, Inc., Maynard, MA (US)

( * ) Notice: Subject to any disclaimer, the term of this patent is extended or adjusted under 35 U.S.C. 154(b) by 282 days.

(21) Appl. No.: 16/506,709

(22) Filed: Jul. 9, 2019

(65) Prior Publication Data

US 2020/0016020 A1  Jan. 16, 2020

Related U.S. Application Data

(60) Provisional application No. 62/695,973, filed on Jul. 10, 2018.

(51) Int. Cl.
 *A61H 3/00* (2006.01)
 *B25J 9/00* (2006.01)
 (Continued)

(52) U.S. Cl.
 CPC .......... *A61H 1/0262* (2013.01); *B25J 9/0006* (2013.01); *A61B 5/112* (2013.01);
 (Continued)

(58) Field of Classification Search
 CPC ............ A61H 1/0262; A61H 2201/165; A61H 2201/5069; B25J 9/0006; A61B 5/112; A61B 2562/0219
 See application file for complete search history.

(56) References Cited

U.S. PATENT DOCUMENTS

| 5,363,025 A | 11/1994 | Colling |
| 8,235,924 B2 | 8/2012 | Bachmann et al. |

(Continued)

FOREIGN PATENT DOCUMENTS

| JP | 2011092507 A | 5/2011 |
| WO | 2010091377 A2 | 8/2010 |
| WO | 2016164395 A2 | 10/2016 |

OTHER PUBLICATIONS

Mooney and Herr; Journal of NeuroEngineering and Rehabilitation (2016) 13:4; "Biomechanical walking mechanisms underlying the metabolic reduction caused by an autonomous exoskeleton", pp. 1-12; Published Jan. 28, 2016.

(Continued)

*Primary Examiner* — Timothy A Stanis
(74) *Attorney, Agent, or Firm* — Barlow, Josephs & Holmes, Ltd.; David R. Josephs

(57) ABSTRACT

The present disclosure is directed to an autonomous exoskeleton device that includes one or more actuators, one or more controllers, one or more sensors with one or more unidirectional transmissions. The control system includes an exoskeleton member configured and arranged on a limb of a user; a control device, a control device connected to the at least one exoskeleton member; an actuator mechanically connected to the limb of the user; and a sensor configured and arranged to sense a global angle of the exoskeleton device relative to the ground. The control device is configured and arranged to use the global angle to control the exoskeleton member.

10 Claims, 18 Drawing Sheets

(51) Int. Cl.
*A61H 1/02* (2006.01)
*A61B 5/11* (2006.01)
*A61F 2/68* (2006.01)
*A61F 2/70* (2006.01)

(52) U.S. Cl.
CPC .............. *A61B 2562/0219* (2013.01); *A61F 2002/6827* (2013.01); *A61F 2002/704* (2013.01); *A61H 2201/165* (2013.01); *A61H 2201/5012* (2013.01); *A61H 2201/5061* (2013.01); *A61H 2201/5069* (2013.01); *A61H 2205/106* (2013.01); *A61H 2205/108* (2013.01)

(56) References Cited

U.S. PATENT DOCUMENTS

| | | |
|---|---|---|
| 8,394,038 B2 | 3/2013 | Ashihara et al. |
| 8,516,918 B2 | 8/2013 | Jacobsen et al. |
| 8,702,811 B2 | 4/2014 | Ragnarsdottir et al. |
| 8,731,716 B2 | 5/2014 | Jacobsen et al. |
| 8,771,370 B2 | 7/2014 | Albrecht-Laatsch et al. |
| 8,852,292 B2 | 10/2014 | Ragnarsdottir et al. |
| 8,894,592 B2 | 11/2014 | Amundson et al. |
| 9,445,931 B2 | 9/2016 | Imaida et al. |
| 2006/0211966 A1 | 9/2006 | Hatton et al. |
| 2009/0222105 A1 | 9/2009 | Clausen |
| 2010/0076360 A1 | 3/2010 | Shimada et al. |
| 2010/0130893 A1 | 5/2010 | Sankai |
| 2010/0256538 A1 | 10/2010 | Ikeuchi |
| 2012/0283845 A1 | 11/2012 | Herr et al. |
| 2013/0012852 A1 | 1/2013 | Imaida et al. |
| 2013/0102934 A1 | 4/2013 | Ikeuchi |
| 2014/0330431 A1 | 11/2014 | Hollander et al. |
| 2015/0142130 A1* | 5/2015 | Goldfarb ............ A61H 1/024 623/25 |
| 2015/0173993 A1 | 6/2015 | Walsh et al. |
| 2015/0209214 A1 | 7/2015 | Herr et al. |
| 2015/0374573 A1 | 12/2015 | Horst et al. |
| 2016/0331557 A1 | 11/2016 | Tong et al. |
| 2018/0200135 A1* | 7/2018 | Tung ................ A61H 1/024 |
| 2018/0325764 A1* | 11/2018 | Yagi ................. B25J 11/009 |

OTHER PUBLICATIONS

Mooney et al., Journal of Neuroengineering and Rehabilitation 2014, 11:151; "Autonomous exoskeleton reduces metabolic cost of human walking"; Published Nov. 3, 2014.

Twist. Merriam Webster Online Dictionary, definition 1C, https://www.merriam-webster.com/dictionary/twist; Dec. 20, 2017.

* cited by examiner

FIG. 15A
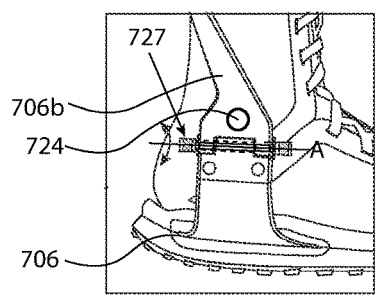
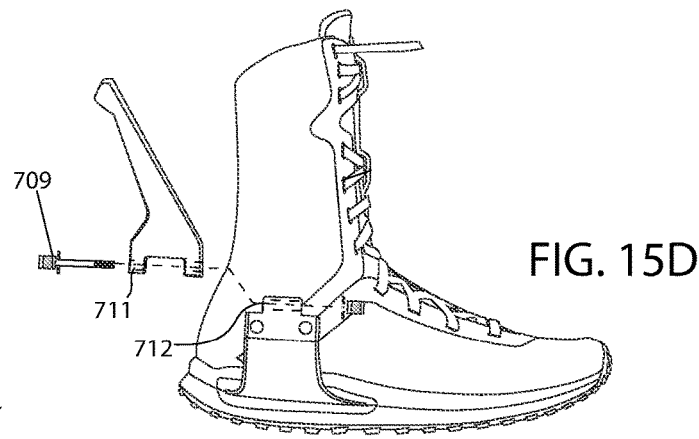
FIG. 15D
FIG. 15B
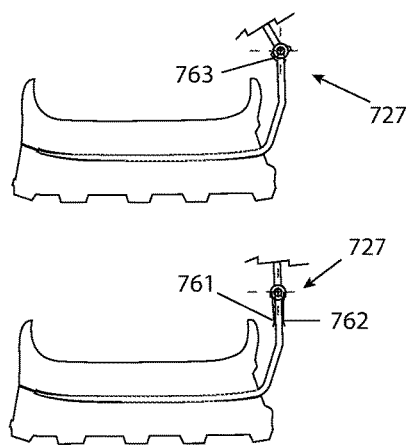
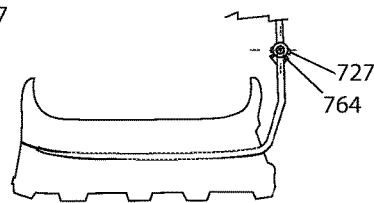
FIG. 15E
FIG. 15C

WEARABLE JOINT AUGMENTATION SYSTEM

CROSS-REFERENCE TO RELATED APPLICATION

This patent document claims priority to earlier filed U.S. Provisional Patent Application No. 62/695,973, filed on Jul. 10, 2018, the entire contents of which are incorporated herein by reference.

BACKGROUND OF THE INVENTION

The invention relates generally to an exoskeleton, a device worn by a person to augment physical abilities. Exoskeletons can be considered passive or active. Passive devices do not require an energy source, such as a battery. Active devices require an energy source to power electronics and usually one or many actuators. It is desirable for exoskeletons to be as lightweight as possible, since the user must carry and move the device along with the body. It is also desirable for these devices to be capable of providing large amounts of force, torque and/or power to the human body in order to assist with motion. These two requirements of low mass and high force/torque/power are often competing requirements and design tradeoffs must be made. Furthermore, it is difficult to apply large forces and torques to the human body. The musculoskeletal system of the human body is capable of sustaining incredible amounts of torque and force, but the exterior of the body is not accustomed to withstanding similar magnitudes of force/torque. Along with being lightweight, and capable of producing high forces/torques/powers, exoskeletons should also be comfortable and efficient at transferring energy to the human. Furthermore, the device should not interfere with the natural range of motion of the body.

It is also desirable for active exoskeletons to be energy efficient and easily controlled. Active exoskeletons require an energy source to power electronics, sensors and usually actuators. Typically, batteries are used with electric motors. However, compressed air can also be used to power pneumatic exoskeletons. The exoskeleton should be as efficient as possible at converting the energy source into useful mechanical force/torque/power. Since the user is often required to also carry the energy source, an efficient device results in a lighter device, a primary design objective. Onboard electronics allow designers to control the exoskeleton, but the device can be mechanically designed to allow for easier control. For example, active devices with a lower transmission ratio are often easier to control and back drive. Output force and torque sensors can also be used to make controlling easier.

SUMMARY OF THE INVENTION

The present invention preserves the advantages of prior art exoskeleton devices. In addition, it provides new advantages not found in currently available exoskeleton devices and overcomes many disadvantages of such currently available exoskeleton devices.

The invention is generally directed to the novel and unique exoskeleton designs that address the problems associated with known exoskeleton devices relating to design challenges of device mass, force/torque/power output, comfort, efficiency and controllability, and the like.

The present invention provides an autonomous exoskeleton that includes one or more actuators, one or more controllers, one or more sensors with one or more unidirectional transmissions. The present invention also provides a mechanical joint in parallel with a biological joint. The exoskeleton device preferably includes an electric motor and a winch, chain, belt, cam transmission or other mechanism for providing unidirectional force. Moreover, a controller, a motor angle sensor, joint angle sensor and/or force sensor may be provided which, in concert, can be used to calibrate the controller for the unique movement of the user in an active or passive mode of the motors. Further still, the motor can be configured to operate in an active mode, whereby the motor is imparting energy to the system, and a passive mode in which the motor is not imparting any, or very little, force to the system. The motor may be any type of motor but is preferably brushless in configuration where its diameter is larger than its length. The present invention can additionally provide for active feedback from system sensors into the controller to alter motor output during active use of the exoskeleton. The present invention, in another aspect, provides for enhanced connection mechanisms between a user's shoes and the remainder of the exoskeleton.

It is therefore an object of the present invention to provide a new and novel exoskeleton device that is compact, lightweight and inexpensive to manufacture yet is powerful and easy to control to address the problems associated with prior art exoskeleton devices.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

FIG. 10A-13 show various exemplary attachment configurations between a footplate and an exoskeleton;

FIGS. 15A-15F show various alternative exemplary attachment configurations between a footplate and an exoskeleton.

DETAILED DESCRIPTION OF THE INVENTION

Certain exemplary embodiments will now be described to provide an overall understanding of the principles of the structure, function, manufacture, and use of the device and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Further, to the extent that directional terms like proximal, distal, top, bottom, up, or down are used, they are not intended to limit the systems, devices, and methods disclosed herein. A person skilled in the art will recognize that these terms are merely relative to the system and device being discussed and are not universal. Moreover, while certain aspects of the instant disclosure are discussed with respect to a leg, a shin, a knee, and a foot of a user, the instant devices and systems can be implemented on any limb of a user.

Figure 1:
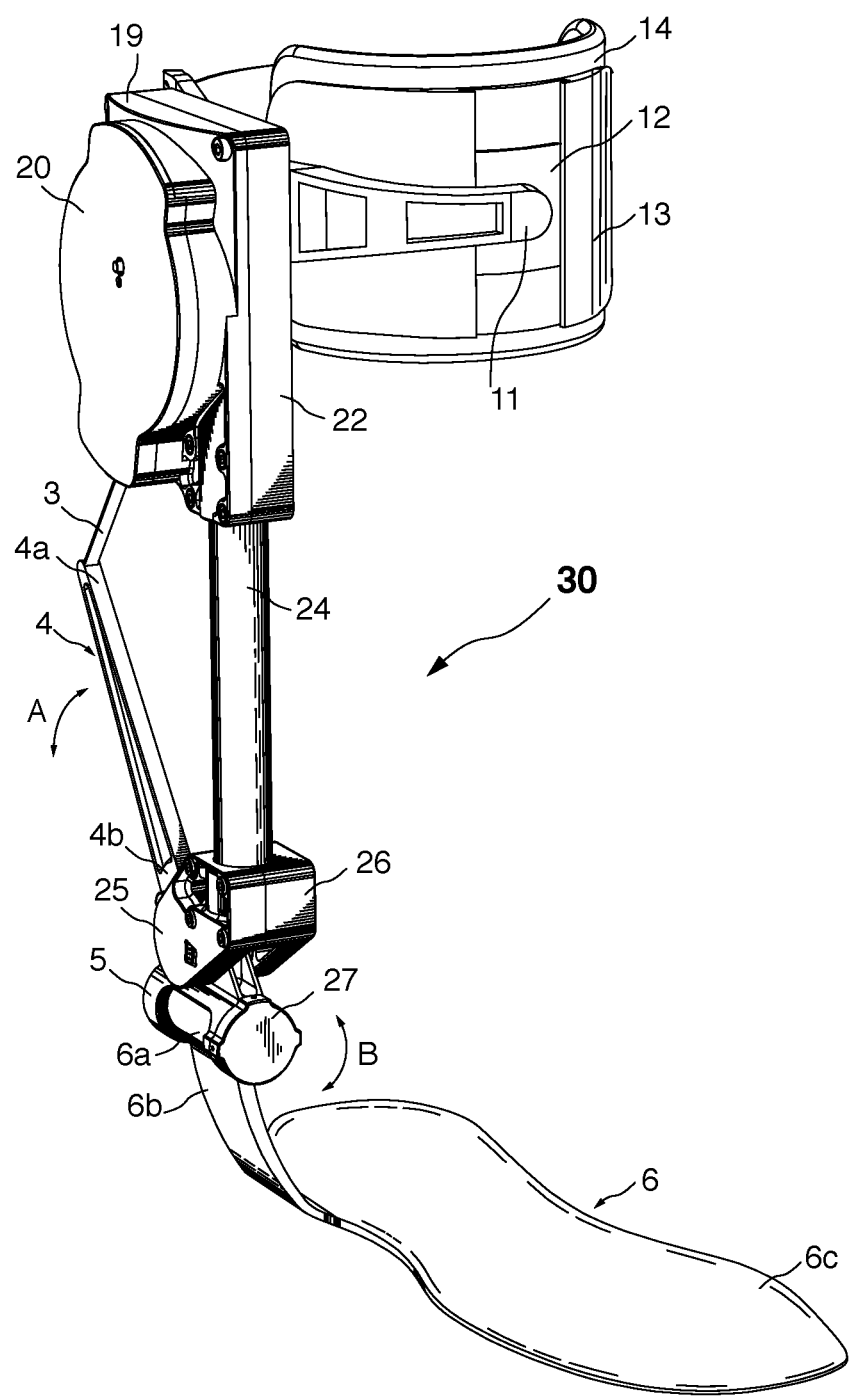
FIG. 1 is a perspective view of one exemplary exoskeleton device.
Figure 2:
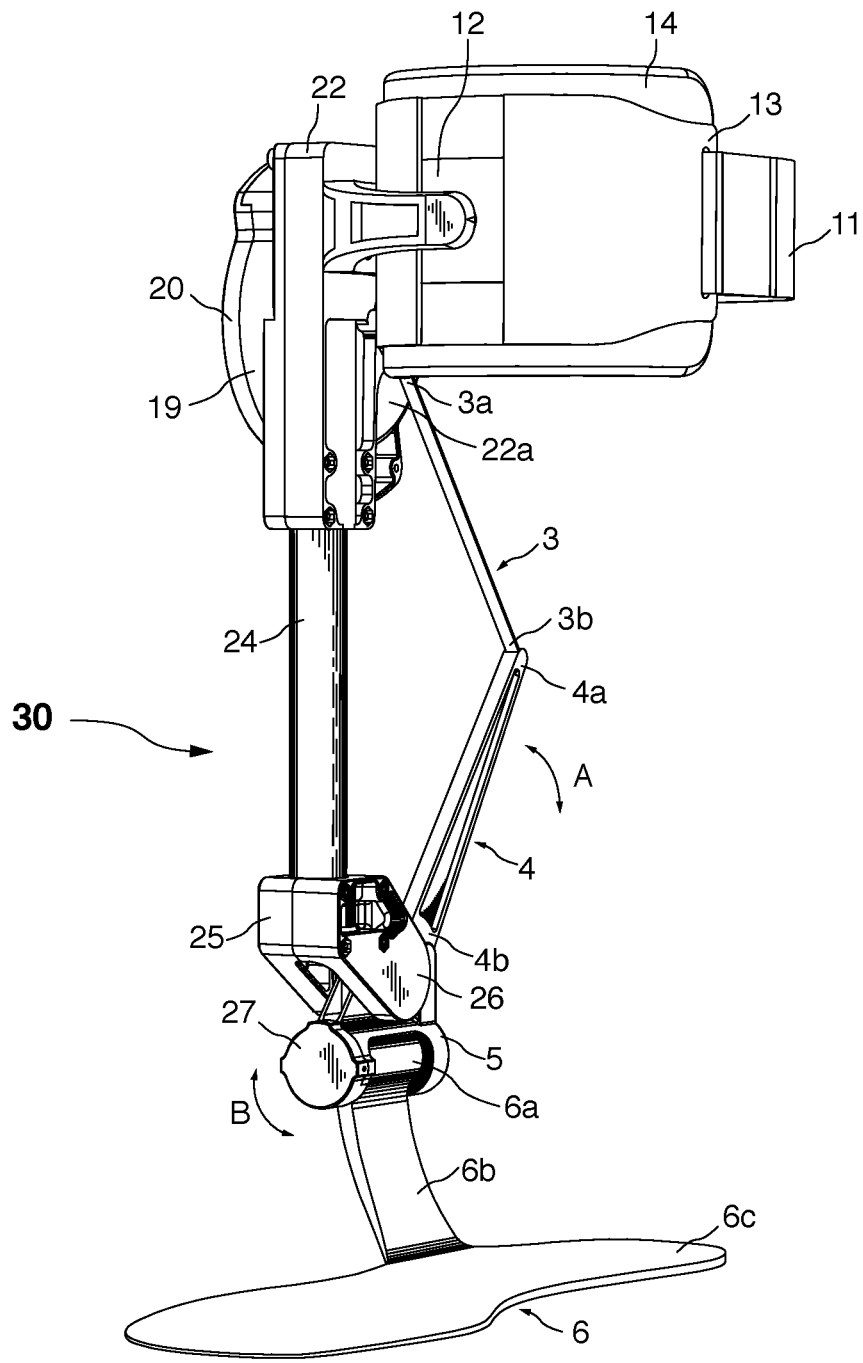
FIG. 2 is a reverse perspective view of the exoskeleton device of FIG. 1.
Figure 3:
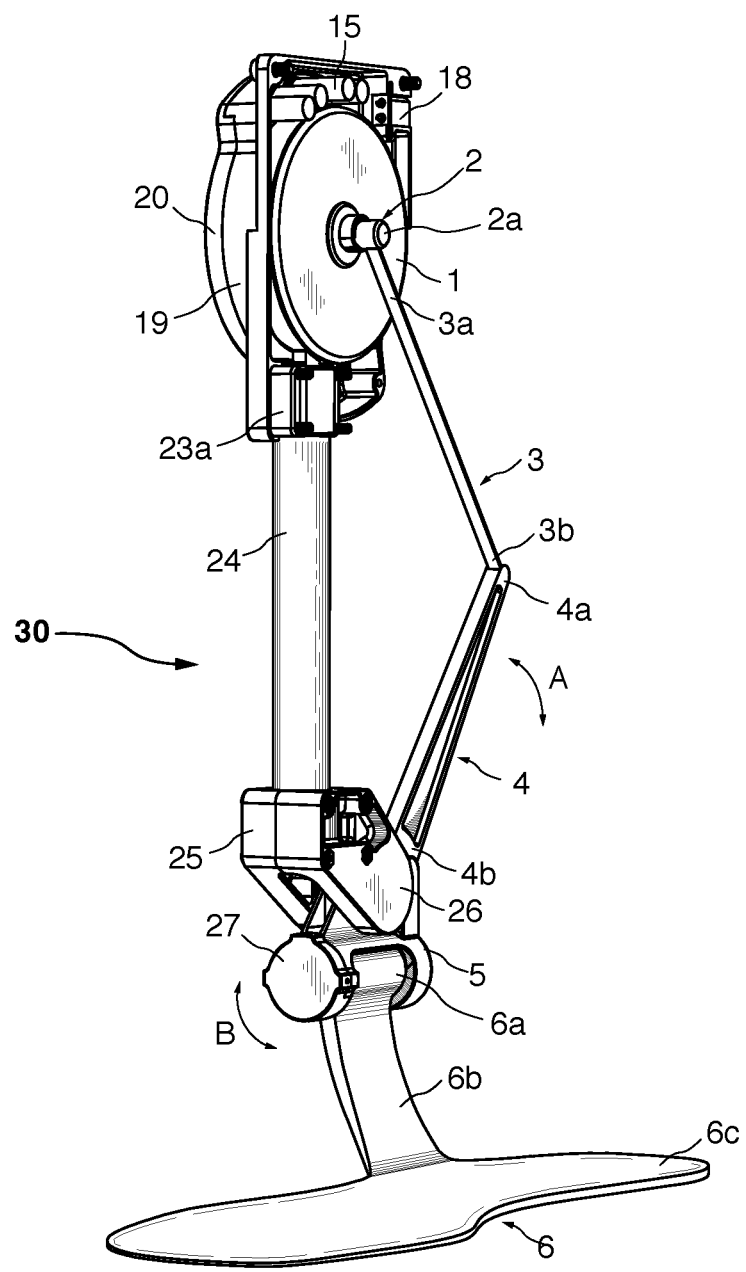
FIG. 3 is a reverse perspective view of the exoskeleton device of the present invention of FIG. 1 with various components removed for illustration purposes to show attachment of the drive belt to the drive spool at an ankle joint.

Referring first to FIGS. 1-4, details of an exoskeleton 30 is shown. FIGS. 1 and 2 show two different perspective views of the exoskeleton 30 from the outside. Details of the different components are shown in FIG. 3 where various components are removed for illustration purposes. The exoskeleton 30 disclosed herein can be substantially similar to that which is disclosed in co-owned U.S. Pat. No. 10,265,195, which is hereby incorporated by reference in its entirety. The discussion of the structure of the preferred exoskeleton 30 are provided herein for perspective alone. The present invention can be used in conjunction with many other, alternative, exoskeletons which are not discussed herein.

Referring to FIGS. 1 and 2, the exoskeleton 30 generally shows a shank tube 24 with a medial ankle joint bearing housing 26 located on the lower end and a medial actuator housing 22 located at the top thereof. As will be discussed in connection with FIG. 2, a motor 1, resides in lateral actuator housing 19 that includes a control electronics cover 20 thereon. Attached to the medial actuator housing 22 is a calf attachment 11 to secure the upper portion of the exoskeleton to a calf portion of the user's leg. The calf attachment 11 preferably includes a shin slide 12 and a shin guard 13 as well as a shin pad 14 for additional custom adjustment for better cushioning and comfort for the user. The components of the calf attachment may be adjusted, as is well known in the art, to provide a tight but not constricting fit.

As a result, this attachment to the upper leg of the user transfers normal forces to the anterior part of the leg, is lightweight, easy and quick to secure and adjust, can adapt to many leg sizes and shapes, has minimal bulk to avoid interference with other pieces of equipment, does not limit range of motion (minimal medial, anterior and posterior protrusions), can be used over pants and is comfortable to the user.

The medial ankle joint bearing housing 26 includes a lateral ankle joint bearing housing 25 the pivotally receives ankle joint cross member 5 therein. The free end of the lever arm 4 is fixed to the joint cross member 5. Therefore, dorsiflexion motion of an ankle joint causes the ankle joint lever arm 4 to move accordingly, namely in the direction A shown in FIG. 2. A composite footplate, generally referenced as 6, has a number of components. It includes a socket portion 6a, a vertical connector portion 6b and composite shank 6c. Eversion and inversion of an ankle joint is permitted by the pivoting action of the rounded free end 6a of composite footplate 6 within ankle joint cross member 5 in a cylindrical shaft and socket type pivoting interconnection 6a, namely in direction B shown in FIGS. 1 and 2.

A lower free end 4b of lever arm 4 is fixed connected to the ankle joint cross member 5 while the upper free end 4a of the lever arm 4 is connected to drive belt 3. The lever arm 4 is preferably angled upwards at a 50-degree angle so that it does not protrude beyond the vertical plane at the back of the heel. This angling also improves the variable transmission profile.

The drive belt 3 is wound up and unwound about a drive spool 2 driven by motor 1, as shown in FIG. 3, which has medial actuator housing 22 removed for illustration purposes. With the housing 22 removed in FIG. 3, control electronics 15 and power jack 18 may be seen residing therein.

Figure 4:
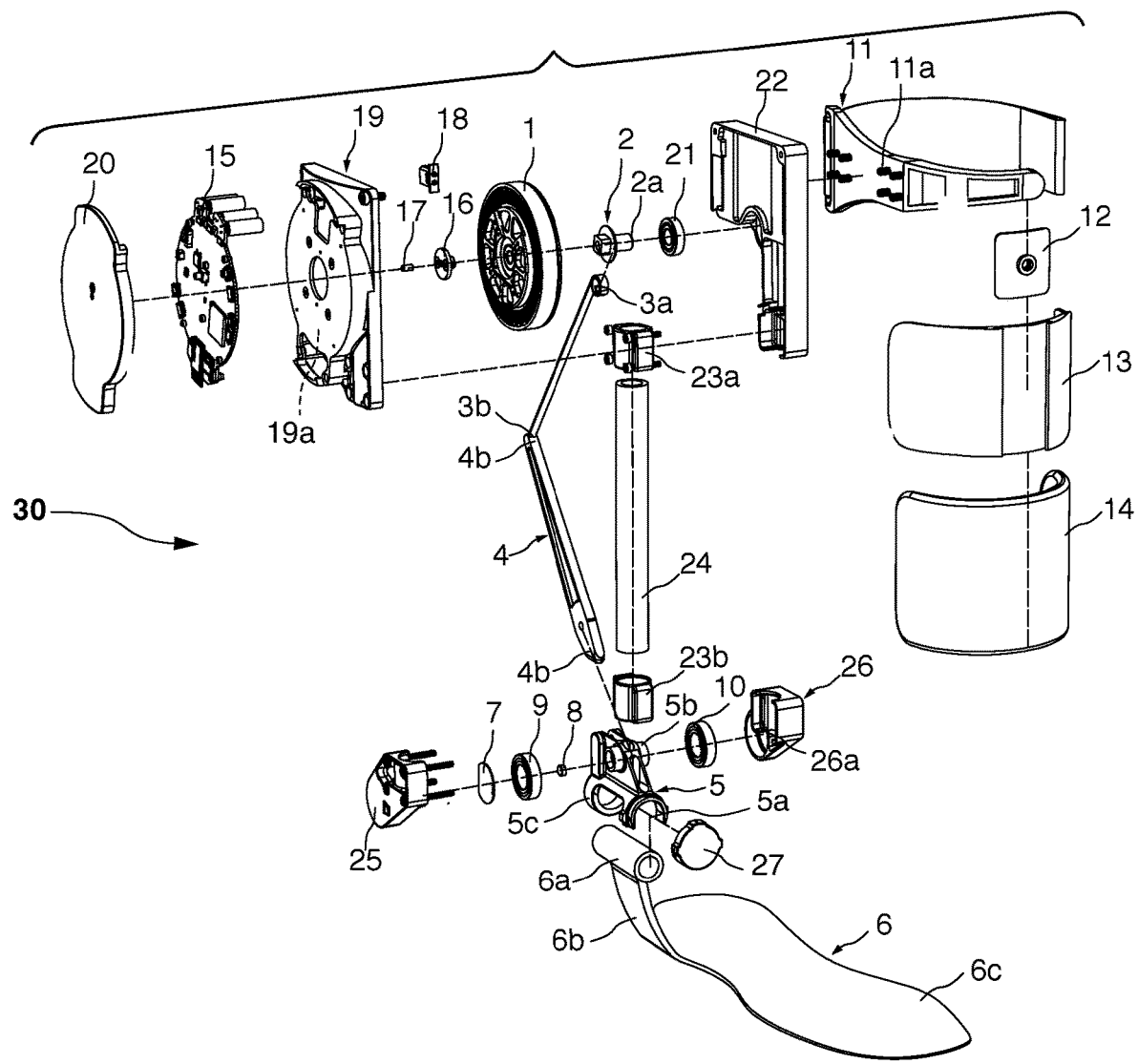
FIG. 4 is an exploded perspective view of the exoskeleton device of the present invention of FIG. 1.

Referring now to FIG. 4, an exploded view of the exoskeleton 30 of the present invention is shown. The ankle motor 1 is mounted between the medial actuator housing 22 and the lateral actuator housing 19, namely, within seat 19a of lateral actuator housing 19. Control electronics 15 are mounted to the exterior surface of the lateral actuator housing 19 and cover 20 is affixed thereon. A motor angle sensor magnet mount 16 is provided to carry motor angle sensor magnet 17. The power jack 18 is mounted to the lateral actuator housing 19 as well. Drive spool 2 is fixed to motor 1 so that rotation of motor 1 rotates the drive spool 2. A medial motor bearing 21 is also provided between the spool 2 and medial actuator housing 22 for improved smooth operation. The free end 2a extends clear of inner face 22a of the medial actuator housing with the free end 3a of drive belt 3 affixed thereto. Thus, as will be described below, rotation of drive spool 2 causes the drive belt 3 to be wound and out as it is being wrapped and unwrapped from about the drive spool 2. The configuration of the drive spool 2 may be modified, as needed. For example, the diameter, length, profile and eccentricity of the drive spool 2 may be modified, as needed to achieve the required winding and unwinding action of the drive belt 3.

The calf attachment 11 is fastened to the medial actuator housing 22 by fasteners 11a. The cushioning shin pad 14, shin guard 13 and shin slide 12 are adjustably interconnected with one another to secure the upper portion of the exoskeleton 30 to the user's body, such as a leg calf. Other structures and configurations may alternatively be used to secure the exoskeleton 30, as desired.

Still referring to FIG. 4, the shank tube 24 includes an upper shank tube ferrule 23A to enable it to be mounted between the lateral actuator housing 19 and medial actuator housing 22. A bottom shank tube ferrule 23B enables the lower portion of the shank tube 24 to be secured between the lateral ankle joint bearing housing 25 and medial ankle joint bearing housing 26.

The ankle joint cross 5 includes a bottom socket 5c and a pivot member 5b at the top thereof. While the shank tube 24 is fixed to the lateral ankle joint bearing housing 25 and medial ankle joint bearing housing 26, the ankle joint cross 5 is pivotally connected to the lateral ankle joint bearing housing 25 and medial ankle joint bearing housing 26 wherein pivot boss 5b sits within seat 26a of joint bearing housing 26 via a medial ankle joint bearing 10. On the opposing side, another pivot boss 5c is provides that pivotally communicates with lateral ankle joint bearing housing via lateral ankle joint bearing 9. An ankle angle joint sensor 7 and ankle angle joint sensor magnet 8 are provided to sense rotational movement of ankle lever arm 4 relative to the shank tube 24 and the user's calf position.

The ankle joint cross also includes a socket 5a to pivotally receive cylinder 6a of composite footplate 6, which also include a connector member 6b and composite shank 6c that may receive a sole of footwear or may be incorporated directly into a sole of footwear (not shown in FIG. 4), as discussed further below. Ankle joint cross cap 27 is provided on the free end thereof. As discussed in FIGS. 1 and 2 above, such a cylinder and socket configuration permits eversion and inversion of the ankle joint. Eversion and inversion movement of the ankle joint and, in turn, eversion and inversion movement of the footwear 32 is permitted due to the cylinder and socket arrangement movement in the direction of the arrows shown.

In some embodiments, a shoe can be specifically designed to interface with exoskeleton, as discussed in detail below. The exoskeleton can apply torques around the ankle joint. In general, the distal structure of the exoskeleton is connected to the shoe and the proximal structure of the exoskeleton can be connected to the lower leg shank. In some embodiments the distal structure of the exoskeleton can be either connected to an existing shoe or directly integrated into a shoe.

Figures 5A, 5B:
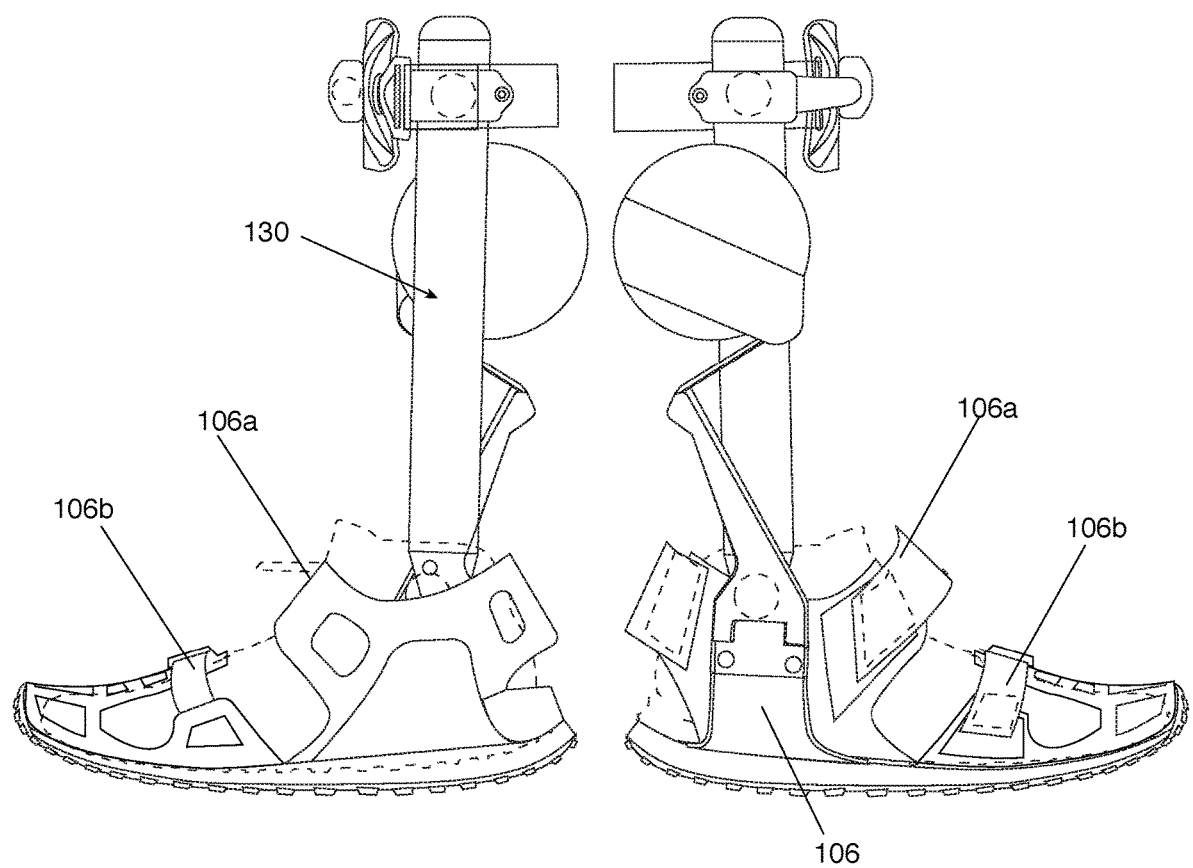
FIGS. 5A and 5B are left and right side views of an exemplary shoe attachment mechanism.

For example, in one exemplary embodiment, as shown in FIGS. 5A and 5B, the distal structure of the exoskeleton 130 can be connected to a footplate 106 disposed in a shoe through a series of removable straps 106a, 106b. A strap 106b may wrap around the toe of the shoe and another strap 106a may wrap around the heel/arch of the shoe. The straps can be oriented to resist the torque produced by the exemplary exoskeleton. A footplate may or may not be included as part of the attachment mechanism.

The distal structure may also attach to the foot at a shoe insert/footplate that goes inside of the shoe, similar to an orthotic insert. The vertical shoe structure may exit the shoe at the footplate through an access hole, not shown, in the shoe. The access hole can include seals that prevent water from the entering the shoe at exit hole. The vertical shoe structure may also exit the shoe through the hole of the shoe where a user inserts their foot. Other attachment strategies include pins and clips, like for bicycle shoes.

Figures 6A, 6B:
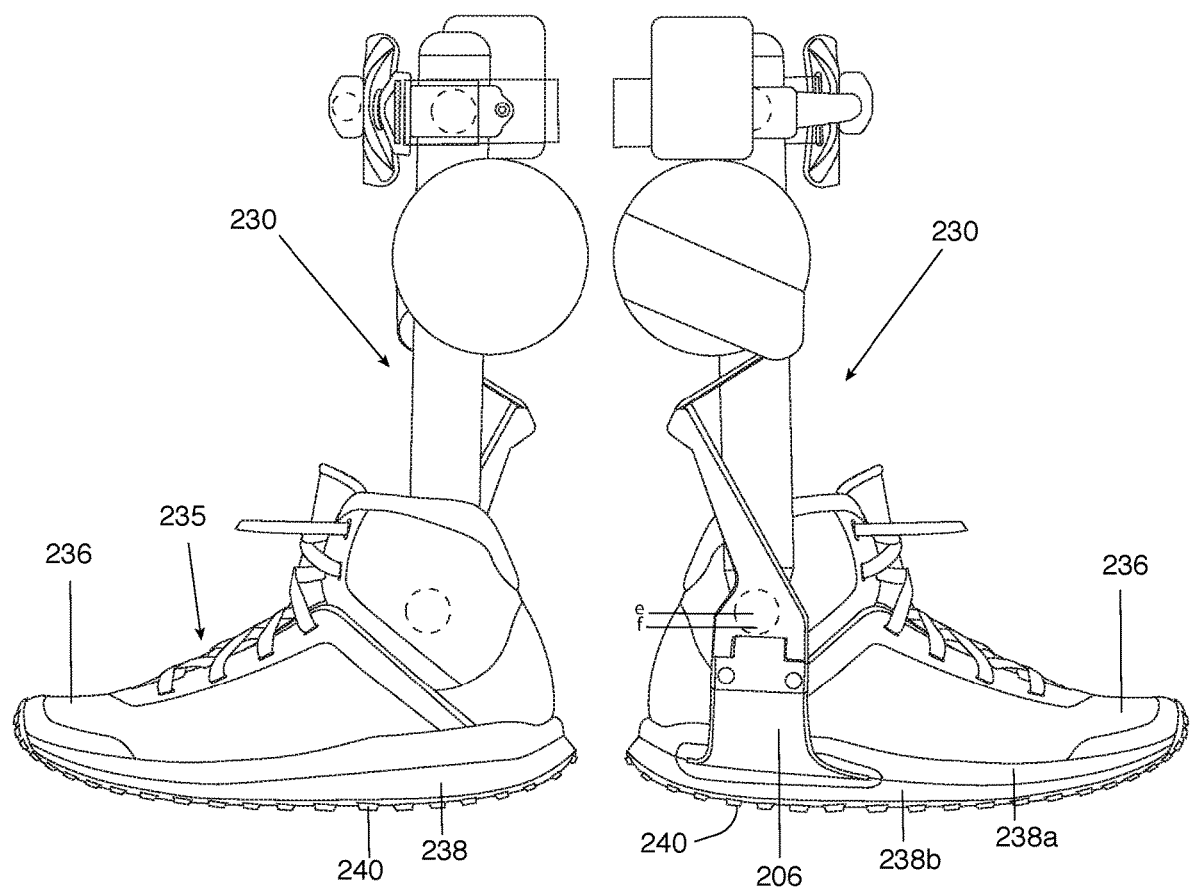
FIGS. 6A and 6B are left and right side views of another exemplary shoe attachment mechanism.

In one exemplary embodiment, the distal part of the structure of an exoskeleton 230 can also be directly integrated into the shoe 235, as shown in FIGS. 6A and 6B. One implementation can use an exemplary composite foot structure integrated directly into the sole of a shoe.

Figure 7A:
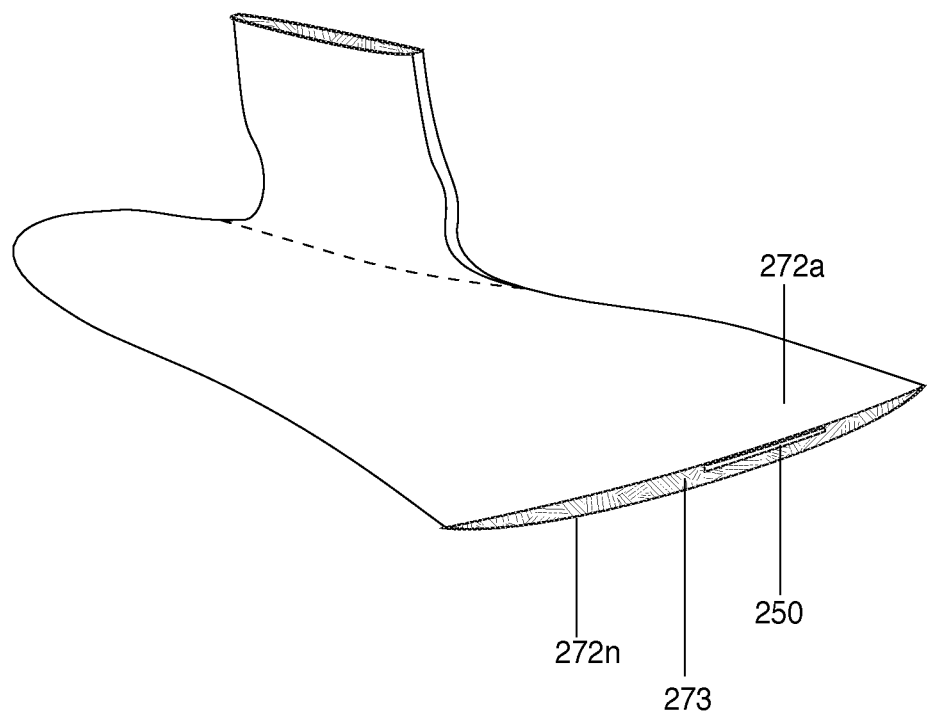
FIGS. 7A-7D are various views of footplate according to an exemplary embodiment.
Figure 8:
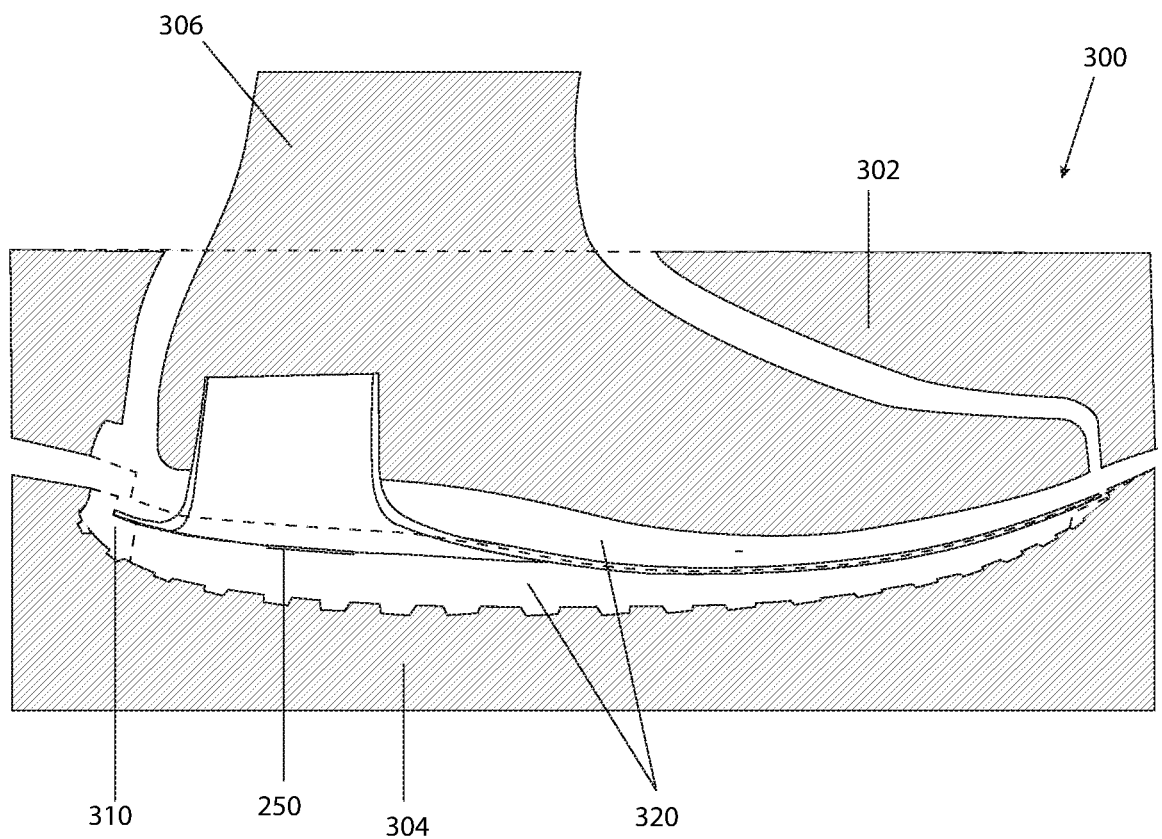
FIG. 8 is a cross sectional view of a shoe sole mold according to an exemplary embodiment.

As shown in FIGS. 6A and 6B, a foam upper midsole 238 is attached to a shoe upper 236. In general, a shoe construction is shown. For example, as shown, a footplate 206 is attached to the distal side of the foam sole 238a and a lower foam midsole 238b is attached to the distal side of the footplate 206. The midsole 238a, 238b material can be other soft conformable materials. The rubber outsole 240 can be attached to the distal side of the lower foam midsole 238b. In some embodiments, sensors 250, as shown in FIGS. 7A and 8, can be disposed between the footplate 206 and the outsole 240 to record needed data for the operation of the exoskeleton. For example, in some embodiments, the sensors 250 can include pressure sensors and an IMU sensor. The sensors 250 can be wired or wireless sensors which can communicate with the central controller for the exoskeleton 230.

In some embodiments, not shown, an alternative footplate can be attached directly to a shoe upper. The lower foam midsole can be attached to the distal side of the footplate and a rubber outsole can be attached to the distal side of the lower foam midsole. In another alternative construction, the foam upper midsole can be attached to a shoe upper, the footplate can be attached to the distal side of the foam sole, and the lower foam outsole can be attached to the distal side of the footplate.

Figure 13:
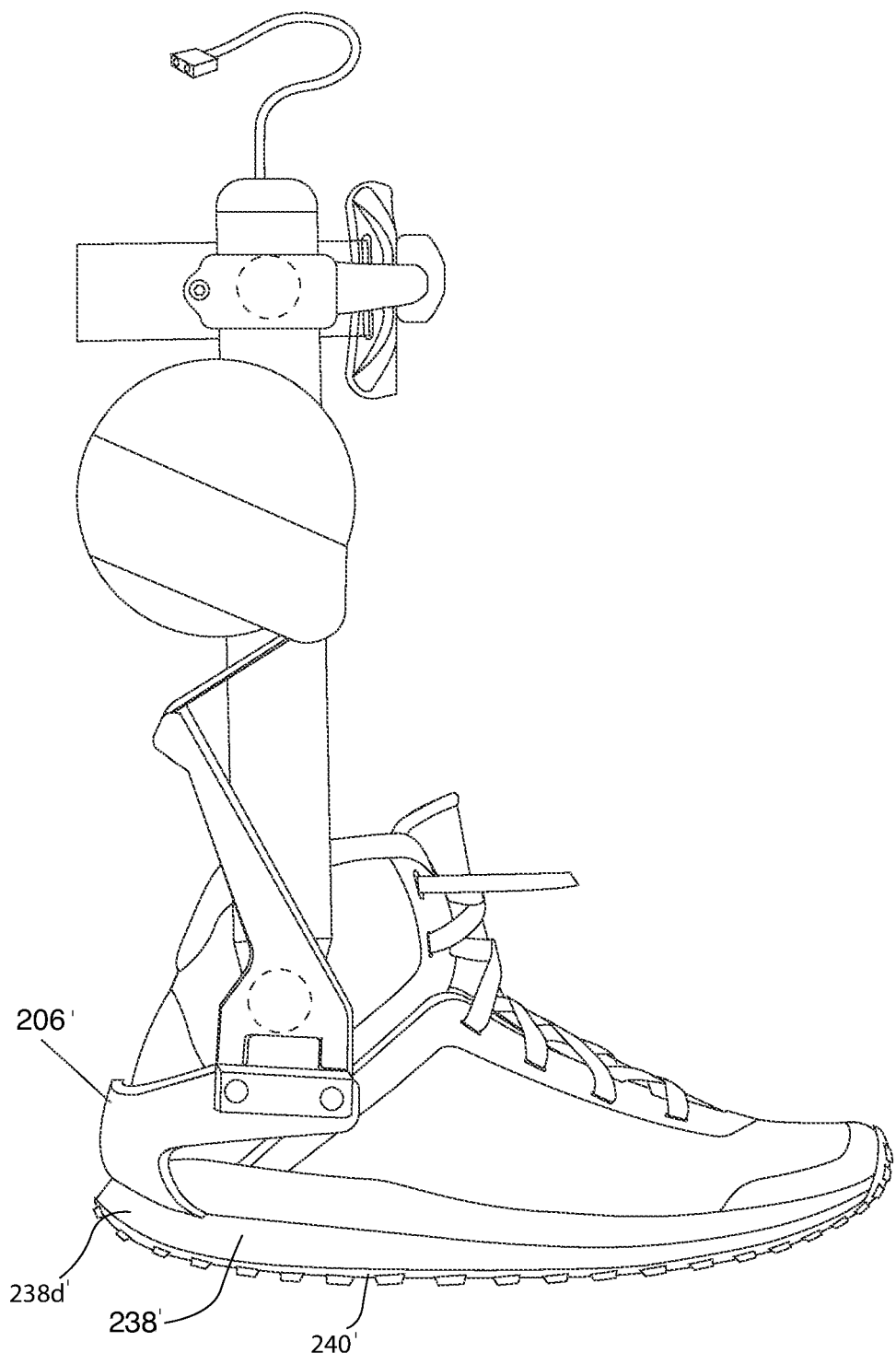

In a further alternative, as shown in FIG. 13, the footplate 206' can be attached to the distal side 238d' of the foam sole 238, and the rubber outsole 240' can be attached to the distal side of the footplate 206'.

Figure 9:
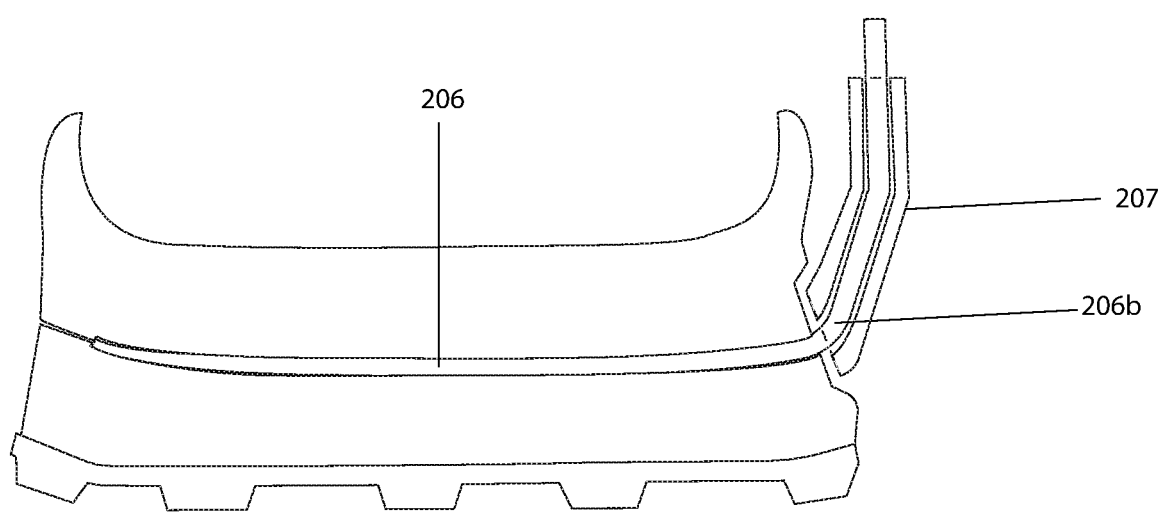
FIG. 9 is a rear view of a shoe and footplate according to an exemplary embodiment.

When used in an exoskeleton, the footplate can also include a vertical foot structure 206b, similar to vertical connector member 6b of FIGS. 1-4, such that the vertical foot structure 206b protrudes from the bottom of the shoe, proximate an upper surface of the outsole 238/240, and extends upwards towards the upper collar of the shoe 235. This vertical foot structure 206b can be part of the footplate 206, as shown in FIGS. 6A-9 or it may be a separate structure that is connected to the footplate in either a rigid, flexible, or jointed manner, as shown in FIGS. 10A-12C. The vertical foot structure 206b may include padding 207, as shown in FIG. 9, to protect both the user's body from the structure or to protect the vertical foot structure from the environment. In one exemplary embodiment, the footplate 206 can include a foam protective pad 207 on the lateral side of a laterally protruding vertical foot structure 206b. The vertical foot structure 206b may also be connected to the footplate 206 in a manner that is easily connected and disconnected, as will be discussed further below. Various fasteners such as pins, magnets, screws, rods and clasps may be used to quickly connect and disconnect the vertical foot structure from the footplate. The vertical foot structure 206b may extend from the footplate on the lateral, posterior and/or medial sides of the footplate, but the lateral side is the preferred implementation.

Figures 7B, 7C, 7D:
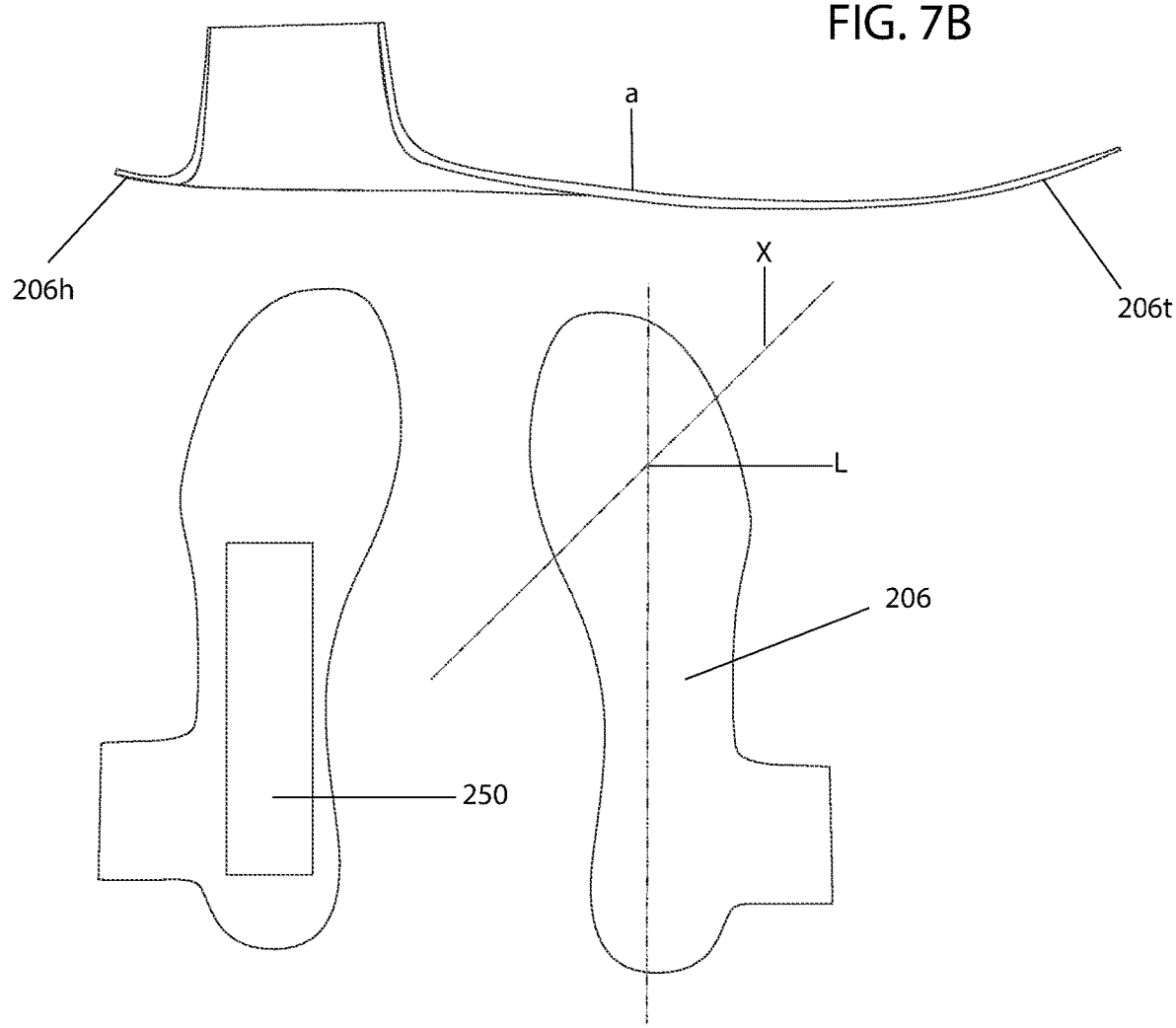

In general, as shown in FIGS. 7A-7D, the footplate 206 can be constructed from multiple layers of composite materials 272a-n. For example, the layers 272a-n can include various carbon fiber, Kevlar fibers, natural fibers and/or fiberglass sheets are adhered with epoxy or any other resin or combinations thereof. The orientation a of the fibers 273, shown in FIG. 7D, can be chosen to create various levels of stiffness in various directions as is needed for various performance needs of the user and specific exoskeleton being used. In the exemplary embodiment, the fibers 273 can be oriented along at +/−45° angle from a longitudinal axis L of the foot plate. The number of layers 272a-n of the footplate 206 can additionally be varied throughout the footplate to create various thicknesses. The geometry of the footplate 206 can be designed to match the shape and curve of the bottom of a foot of a user. The footplate 206 can be curved upward at the heel 206h and toe 206t, as shown in FIG. 7B. In some embodiments, the toe of the footplate can be thinner to maintain flexibility.

Other design considerations can be used to affect the performance of the footplate 206. For example, layer(s) 272*a*-*n* of unidirectional fibers 273 can be used to increase strength along certain directions. Further, the layers of woven fibers 273 can be used to increase torsional strength along certain directions. In a preferred embodiment, the vertical foot structure 206*b* and footplate 206 are a single composite piece. Layers of woven fiber 273 can be used on the vertical foot structure 206*b* to increase torsional stiffness about a vertical axis. Layers of unidirectional fibers 273 can be used in the footplate to increase strength. In some embodiments, the fibers 273 can also be oriented to run from the top, posterior edge of the vertical foot structure to the medial metatarsal joints. In this alternative embodiment, the fibers 273 can promote efficient load transfer from the vertical foot structure to the footplate when a plantar-flexion torque is applied about the ankle joint. In one exemplary embodiment, the heel 206*h* of the footplate 206 can be approximately between 1-4 mm thick and the thickness of the toe area 206*t* of the footplate can be approximately 0.3-2 mm thick. The range of thickness can be approximate, or substantially in the recited range within an acceptable manufacturing tolerance of +/−0.1 mm. The acceptable tolerances in thickness can allow for slight variation above or below the acceptable thicknesses that may occur as a result of machining or wear.

In one embodiment the footplate 206, or a part of it, can be a stack of thin carbon plates, not shown. The stack can be changed to obtain more or less stiffness or to change how the forces are transferred. For example, three, or more, layers can provide a stiffer footplate, where one or two layers would be less stiff. The stack can be customized at the factory, or by the user to ensure that the footplate conforms with necessary performance specifications. The customizations can be user defined or can be determined with a second device which can scan the geometry of the user's feet or the device can scan the range of motion of the user's feet during different situations, such as walking, running, jumping, lifting, climbing stairs, etc, or combinations thereof. In some instances, the thin plates can be bonded together. In others they will not be glued. The stack will be placed in the shoe, under the insole.

In some embodiments, as shown in FIG. 8, a footplate 206 having at least one sensor disposed thereon, can be assembled into a sole 320 of a shoe. The process can include the use of a mold 300 having an upper plate 302 and a lower plate 304. The upper plate 302 and lower plate 304 can come together to form a cavity with a foot shaped mold 306 to form the upper and mid-soles of the shoe. The mold 300 can additionally include a structure 310 that is configured to hold the footplate 206 during the molding process. The mold can be filled with any desired flowable material.

The variety of variations on the footplate disclosed herein can be used with any of the following connection mechanisms described for connecting the footplate with the lower structure of the exoskeletons. In some embodiments, plural connections types, or mechanisms may be used to facilitate the use of a plurality of exoskeleton types.

Figures 10A, 10B:
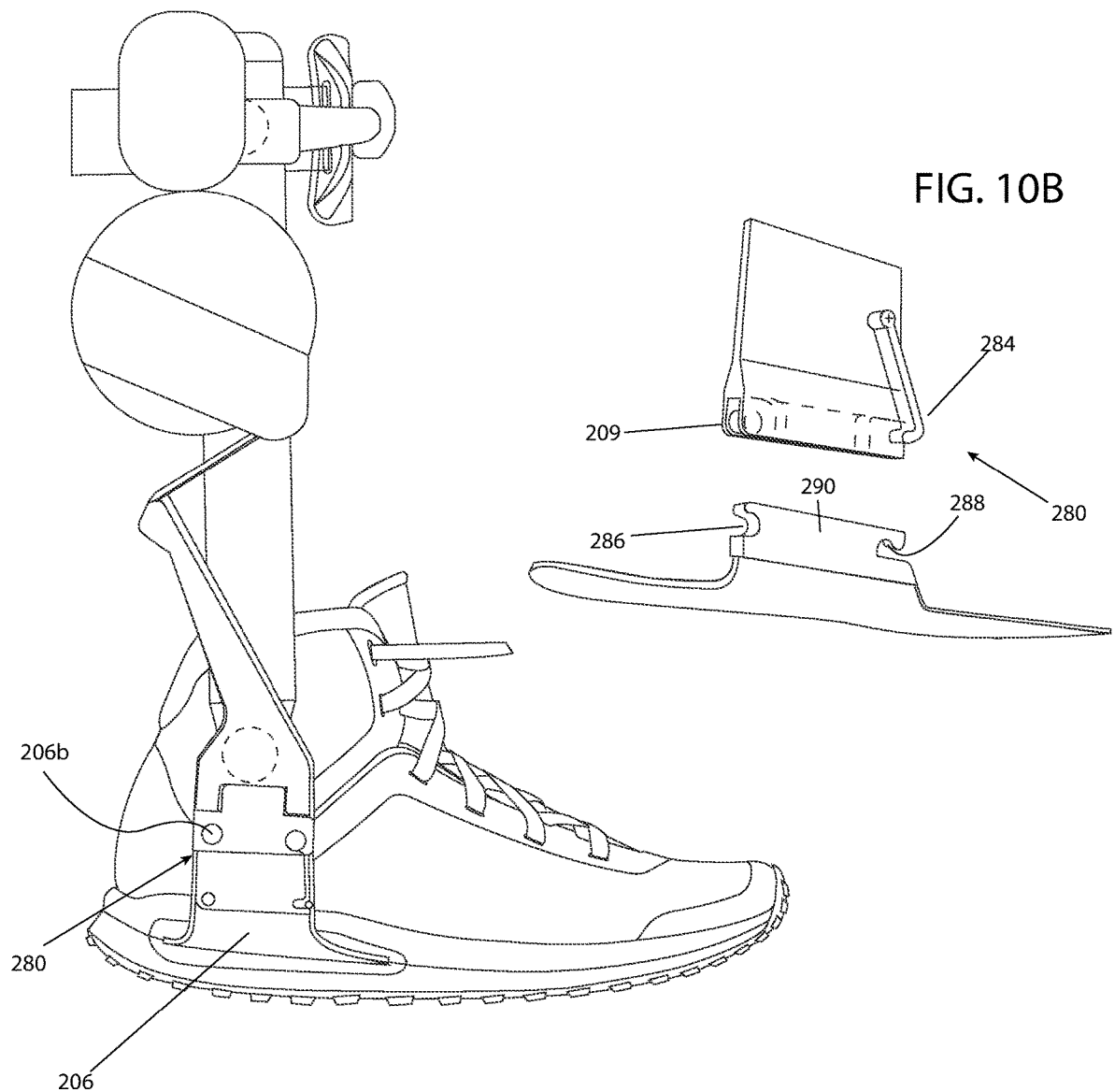

In some embodiments, as shown in FIGS. 10A-12, the vertical foot structure 206*b* can be connected to the footplate 206 in a manner that is easily connected and disconnected. As shown in FIGS. 10A and 10B, the connection mechanism 280 can include at least one pin 209, on the vertical foot structure 206*b*, that can be received in a cutout 286 on the footplate 206, and the vertical foot structure 206*b* can be rigidly connected to the footplate 206 by means of a clasp or collinear hole 284 received in a cutout 288. The pin 209 can be inserted into the cutout 286 first, then the clasp can be engaged into the cutout 288 to lock the vertical foot structure 206*b* to the footplate at an engagement location 290.

Figure 11:
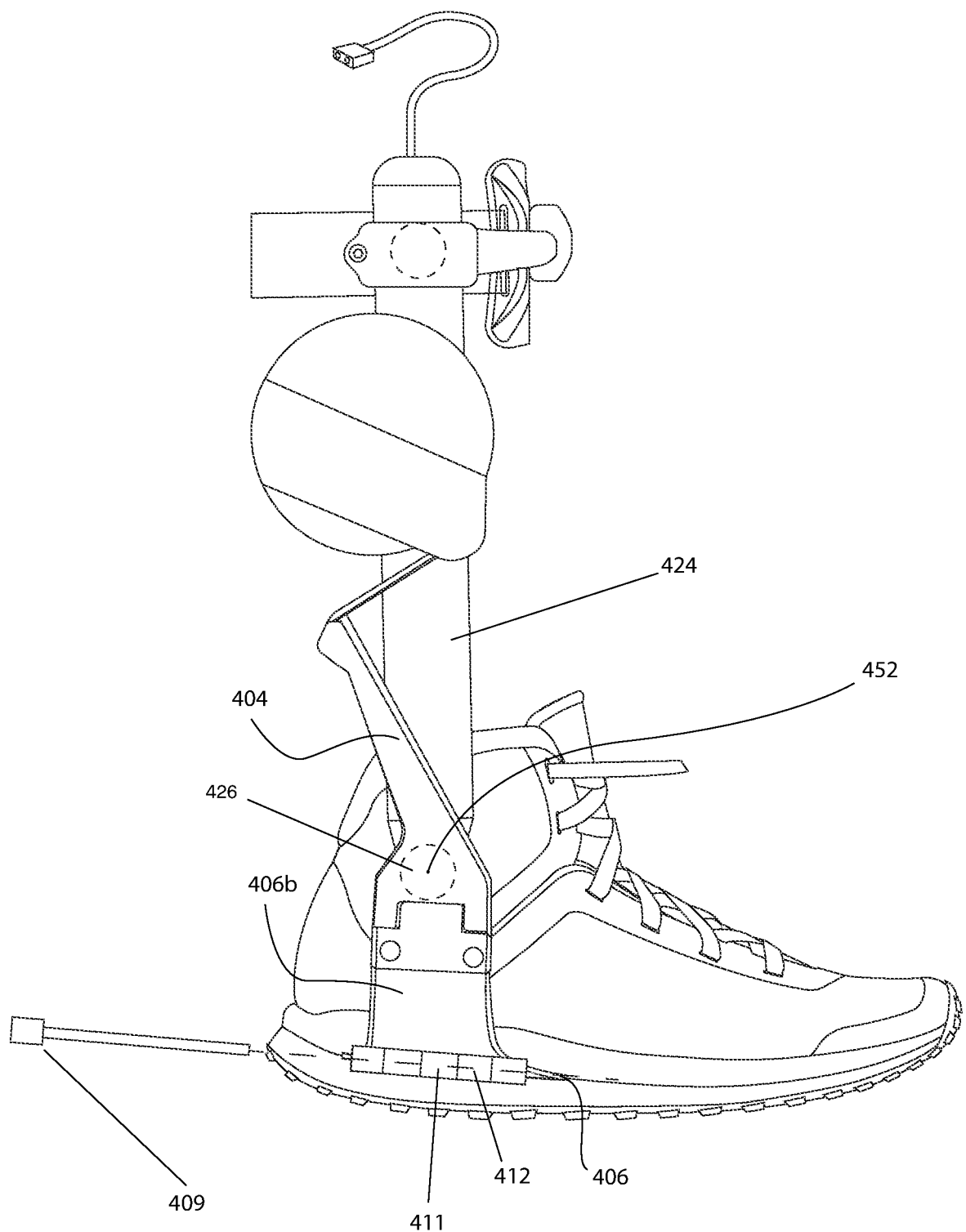
Figure 12A:
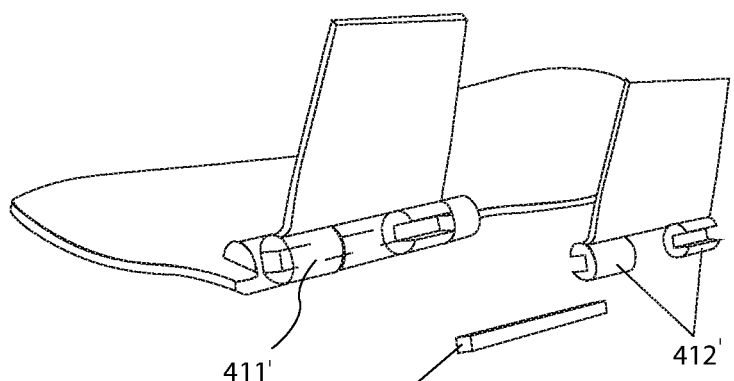
Figure 12B:
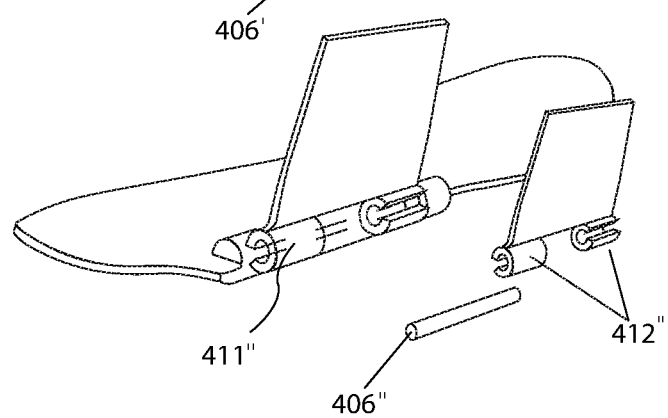

In an alternative embodiment, as shown in FIG. 11, a footplate 406 can include one or more horizontal pins 409 that run in the anterior-posterior direction along the lateral side of the footplate 406. While similar, but different, reference numerals are used herein, the remainder of the structure of the exoskeleton and the shoe can be substantially the same as other embodiments disclosed herein. Similar to the exoskeleton 30 of FIGS. 1-4, the medial ankle joint 426 can be actuated, or pivoted by a free end of the lever arm 404 is fixed to the vertical structure 406*b* to pivot the footplate 406 relative to the shank tube 424 about the pivot point 452. The pins 409 may have a circular or non-circular cross section. The pins 409 may allow for relative rotation between the vertical foot piece 406*b* and the footplate 406 by inserting the pin 409 into the circular pin receiving portions 411, 412 of the vertical foot piece 406*b* and the footplate 406, respectively. In some embodiments, the hinge can be similar to a traditional door hinge. In FIGS. 12A and 12B, alternative pin shapes 406', 406" and hinge shapes 411', 412', 411", 412", are shown. The pins 406, 406', 406" may also be screws. If the pins 406, 406', 406" are removeable, then the vertical piece 406*b* may have a corresponding hole to receive the pins and connect to the footplate 406. If the pins 406, 406', 406" are permanently attached to the footplate, then the vertical foot structure may use articulated clasps or a twist-on mechanism to attach to the pins. In one preferred embodiment, the vertical structure can be inserted and removed from the footplate when the vertical structure is in one orientation and is affixed to the footplate when in the worn orientation. For example, the vertical foot structure 406*b* can be attached or removed from the footplate 406 when the vertical foot structure 406*b* is parallel with the ground. The act of twisting the vertical foot structure upwards results in it locking into the footplate.

In one embodiment, the footplate can have receiving holes and the vertical foot structure has corresponding pins. The pins of the vertical foot structure slide into the corresponding footplate holes in a direction that is orthogonal to the forces exerted by the exoskeleton. As noted above, the footplate and vertical foot structure may also have sensors embedded or attached to them. These sensors may include inertial measurement units, pressure sensors, strain sensors, force sensors. These sensors may also contain their required power sources and wireless communication capacities, they may scavenge energy, or they may be connected via wires to the control system of the exoskeleton.

There are various methods to manufacture the footplate, as discussed above. The shape and thickness of the footplate may be determined by the direct measurement of a subject's foot, either by the user (phone app) or by a company employee (phone app, 3D scanner, mechanical measurement, etc.). The adhesive or materials in the footplate may also be conformable when heated and shape stable during operating conditions. A footplate could be heated and worn by a user to achieve the desired shape. The cooled footplate would then maintain the desired shape during use. In some instances, the heat molding process can be done multiple times to accommodate changes in user's physiology, preferences, or to fit a different user.

Another method of manufacturing the footplate can use a core. A core could be 3D printed or manufactured using another process. Rapid, digital processes are favored. The composite laminated would then be adhered to the surface of the core. The core provides both strength by increasing the area moment of inertia, along with providing a shape to form the composite layup. Furthermore, conformable bladders of fluid could be used to press the curing composite against the core. In some instances, the core can be dissolved before use, leaving a hollow composite structure.

Along with acting as connection point for the vertical foot structure, the footplate can provide protection and passive energy storage. The rigidity and strength of the footplate can be used to protect the bottom of the user's foot from protruding objects, such as rocks and edges. It can act as a rock plate and as a stabilizer. The elasticity of the footplate can also be used to store and release energy during the gait, as shown with respect to FIG. 15F.

Figure 15F:
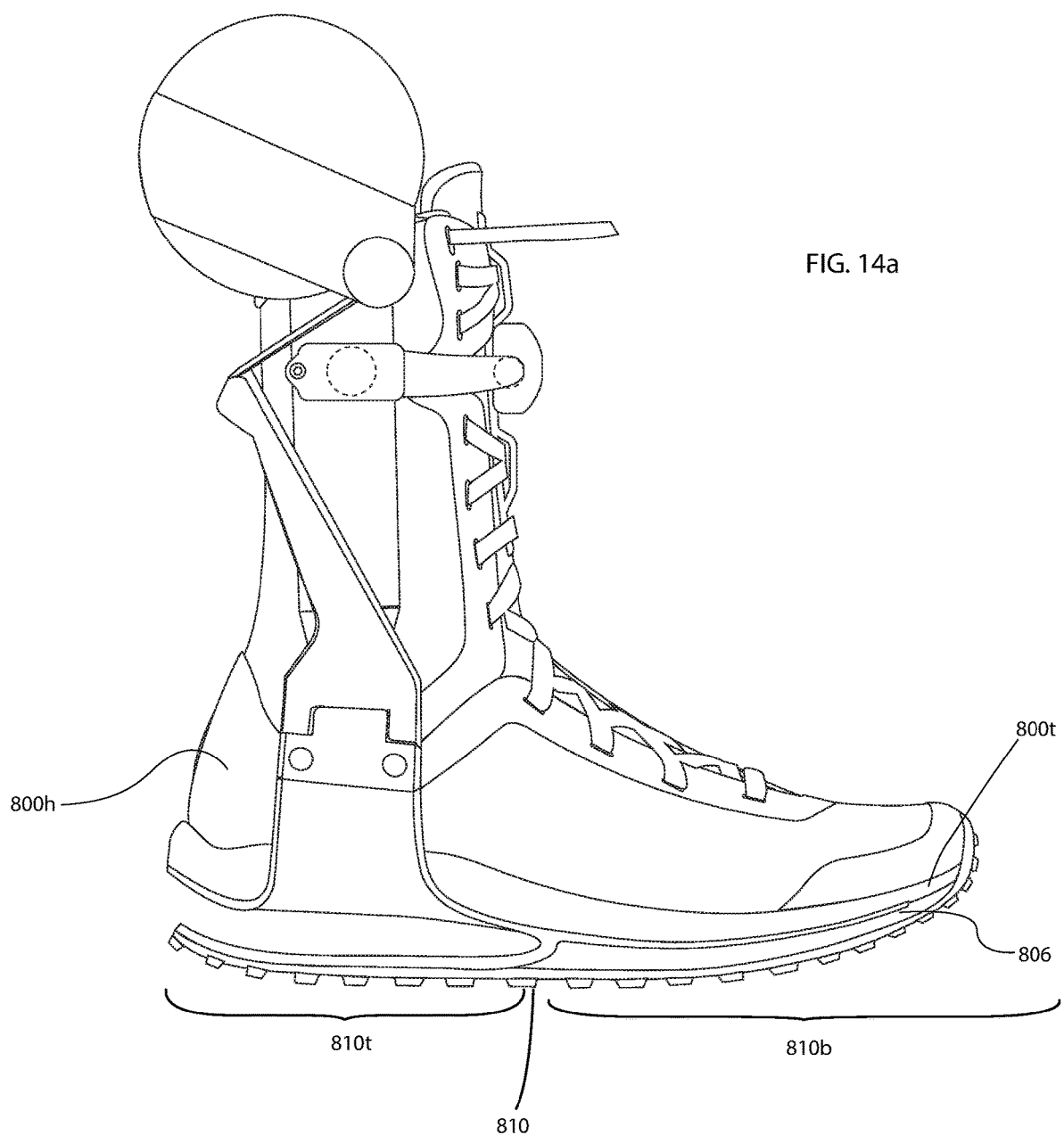

As shown variously in FIGS. 15A and D, the vertical foot structure 706b may only be attached to the footplate 706 and actuator (not shown in FIGS. 15A-E), or as in the preferred embodiment, the vertical foot structure 706b can be attached to a mechanical joint that mimics the range of motion of the human ankle, as shown in FIG. 11. Such a mechanical joint can be similar to the one shown in FIGS. 1-4. In one embodiment, the vertical foot structure 706b can be connected to the ankle joint structure 724 through a first rotational joint 727 with an axis of rotation A non-parallel to the plantarflexion/dorsiflexion axis of rotation, such as the eversion/inversion axis of rotation. The ankle joint structure 724 can then connected to the leg structure through a second rotation joint with an axis parallel to the plantarflexion/dorsiflexion axis of rotation, not shown in FIGS. 15A-F. The first joint 727 may be a low friction joint, or it may have designed friction. The friction in the first joint may also be adjustable to resist motion, via tightening of pin 709 disposed in the hinges 711/712. The first joint 727 may use a plurality of bearings and have a mechanism to quickly disconnect the vertical foot structure from the ankle joint structure. The first joint 727 may be a screw 709 that can be tightened or loosed to adjust the joint friction. The first joint may also be flexural. The first joint may implement springs 761, 762, as shown in FIG. 15C, or dampers to affect the torque about the joint in a passive manner. The first joint 727 may also include a hard stop 763 that limits the maximum angles of rotation, as shown in FIG. 15B. These hard-stops may include soft bumpers 764, as shown in FIG. 15E, that reduce the acceleration when hitting the hard stop. The first joint may also include sensors to measure forces or angles of rotation.

In a preferred embodiment, the second joint is free to rotate and designed to minimize friction. The second joint may also implement dampers and or springs during part or all of its range of motion. For example, springs may be integrated across the second joint to only impart a force during certain angular ranges. The second joint also has sensors to measure the angle displacement between the ankle joint structure and the leg structure. The second joint may also implement hard-stop features to protect the foot from being over-extended.

The ankle joint structure also connects to the actuator to impart forces between the ankle joint structure and the leg structure. The actuator is connected to the ankle joint structure at a point that is non-coincident with either the first joint axis or the second joint axis of rotation. Forces from the actuator impart a torque about one or both joints of the ankle joint structure.

Figures 14A, 14B:
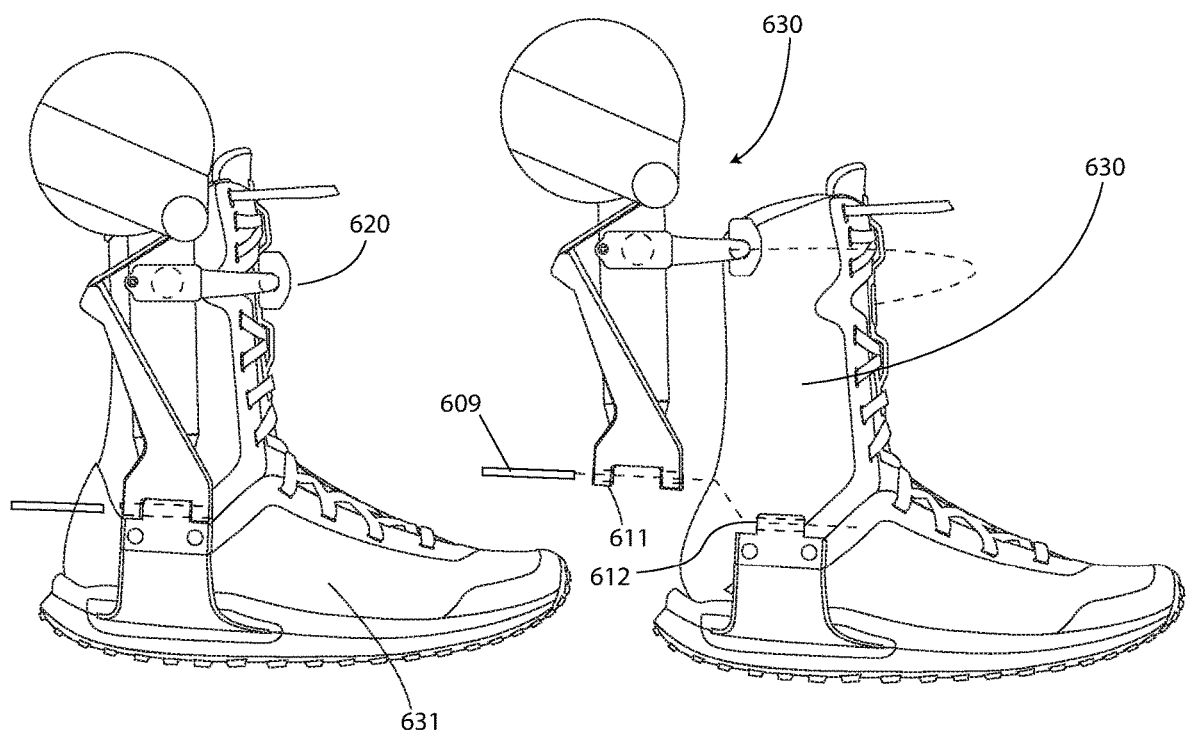
FIGS. 14A & 14B are side views of an exemplary alternative shoe embodiment.

The leg structure may be attached to the shin or connected directly to the upper part of the shoe, such as the tongue of the shoe, as shown in FIGS. 14A and 14B. For example, the shoe 631 can have an extended shaft 633 that extends upwards towards the knee of the user. The shoe 631 in this embodiment can have the exoskeleton 630 directly attached thereto through shin attachment mechanism 620 and a similar connection mechanism between the exoskeleton 630 and the vertical foot structure 606b. While a pin 609 and hinge 611, 612 are shown, any of the aforementioned connection mechanism can be used. The leg structure may also be attached to the lower leg through a series of joints that allow for motion in directions orthogonal to the force created by the actuator.

Figure 16:
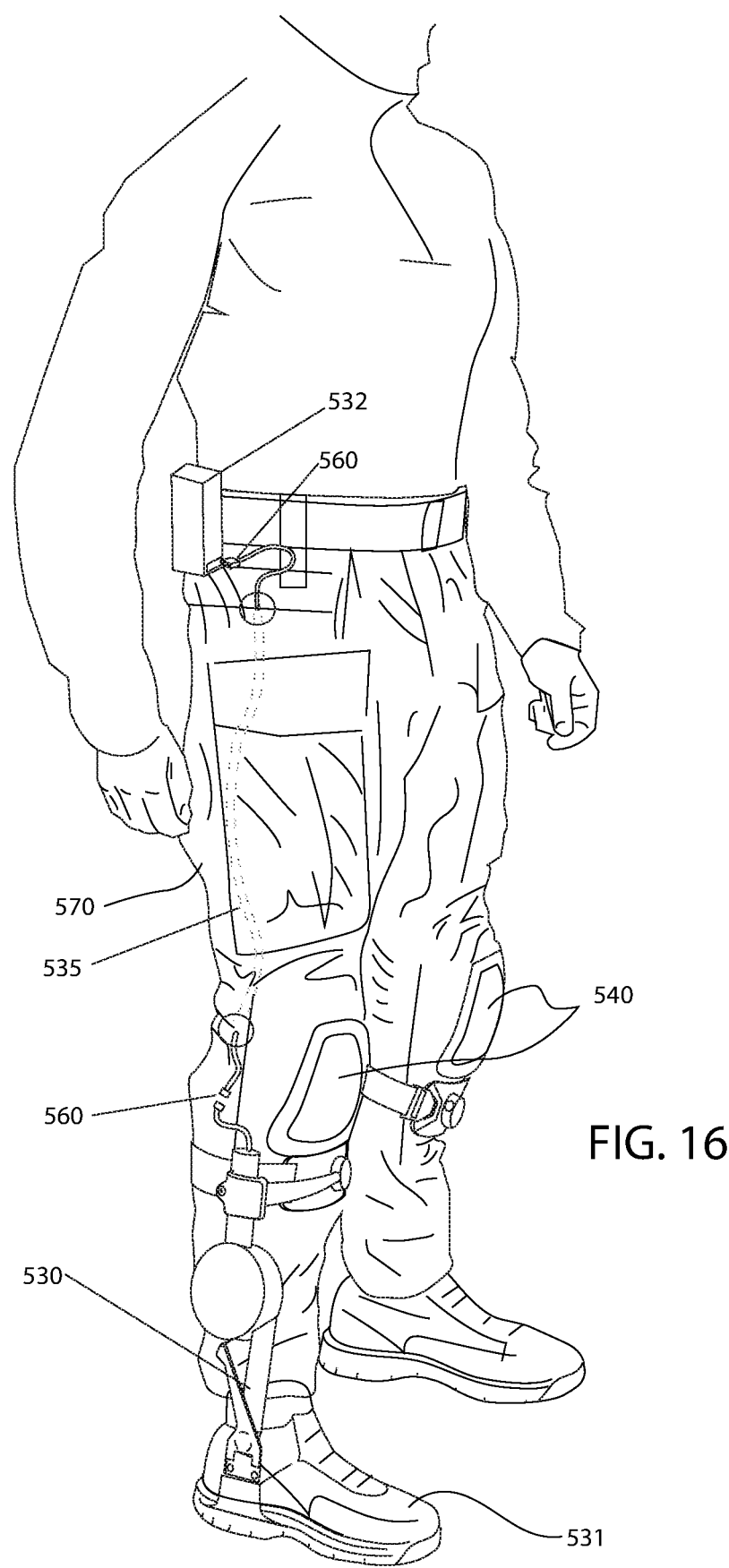
FIG. 16 is a perspective view of an exoskeleton system worn by a user.

Protective pads 540, as shown in FIG. 16, can be integrated in the leg structure of the exoskeleton 530 to maintain the user's ability to kneel and crawl. A skid plate may be integrated in the shoe to make certain bodies of the exoskeleton slip instead of directly impacting the malleolus.

As shown in FIG. 15F, the footplate 806 may also include additional features that allow for the storage and release of energy. An additional composite leaf spring 810 can be integrated into the footplate 806 that stores energy during heal strike 800h and releases the energy at toe off. The spring 810 may look like a horizontal 'Y' with the top of 'Y' 810t under the heel 800h and the bottom of the 'Y' 810b under the toe 800t. The arms of the 'Y' are elastic and can be compressed. The elastic footplate 806 may be manufactured as a single composite piece or as separate pieces that are adhered in a separate process.

It is also an important aspect of the present invention to consider the attachment of an exoskeleton's 530 battery 532. The battery 532 may be integrated into the main structure 530 (attached to the structure, integrated in the composite tube, etc.), or into the shoe 531 (upper part of the shoe, as part of the sole, etc.) but to decrease distal mass the battery 532 may also be worn on a different location on the body. In one embodiment, the battery 532 can be worn in a backpack or around the waist, as shown in FIG. 16. Power cables 535 can connect the battery to the exoskeleton, via a connection mechanism 560. The central pack 532 may also include additional computing hardware and the cables 535 may also include additional data wires. These cables 535 can we worn outside the pants 570, inside the pants, or integrated into the pants. Conductive thread or other wearable conductive textiles can be directly integrated into the clothing to both power and connect the exoskeleton with the battery. Additional channels can also be sewn into the clothing to provide a conduit for connecting wires. In some embodiments, more than one batteries 532 can be used so that they can be interchanged without disrupting the power to the exoskeleton 530. One might be mounted at the waist, and each exoskeleton can have a small battery in it.

There are various methods for charging the batteries 532, as shown in FIG. 16, of an exoskeleton, such as the exoskeletons disclosed herein. The batteries may be removable and charged in a separate unit. Such a configuration can allow for the rapid replacement of batteries and ability to reduce down time. A charging port may be used on the exoskeleton to charge the batteries while integrated. Wireless charging may also be possible under certain circumstances. For example, the exoskeleton may include an inductive coil or other wireless charging mechanism that can receive power while a user is sitting in a car or at a desk. In some embodiments, the controller of the exoskeleton can be programmed such that, upon engaging a wireless charging system, the actuators are required to be in an inactive state. For example, if a wireless charger is integrated into a vehicle's seats, or other structure such as a chair, for charging while the user is driving, the master controller of the exoskeleton will, advantageously, ensure that the actuators are in a passive mode so that the operation of the vehicle is not impeded. For example, if the actuators were to activate during the operation of a vehicle, the gas pedal might be pushed too far and the vehicle might undesirably accelerate causing an accident. In other situations where non-contact wireless charging occurs, such as non-contact wireless charging occurring in a warehouse or factory, the actuators of the exoskeleton may continue to operate in an active mode. In some embodiments, certain electronic tags, e.g. RFID tags, can instruct the controller to engage an active or inactive mode of the actuators depending on the needs of the user in that environment. For example, an RFID tag in a vehicle may instruct the controller to disengage the actuators for reasons discussed above. On-board power electronics can also be used to accept a wide range of charging voltages, such as 12 V from a car. Alternatively, the on-board power electronics can be designed to accept any charging voltage.

In operation, actuators for an exoskeleton must be efficient and capable of producing large torques. As discussed above, the actuators can include an electric motor that uses a transverse-flux magnetic topology. The motor may also implement advanced materials such as graphene or nanotube conductors.

In some embodiments, the exoskeleton can be developed to be modular in construction. For example, a separate ankle exoskeleton module and a knee exoskeleton module can be designed independently. If worn at the same time, the two systems can be both mechanically and/or electrically attached to transmit forces and/or information and electric power between them.

Certain exoskeleton systems can use a transmission that includes a lever arm to increase the torque at the joint, as shown in FIGS. 1-4. Such a lever arm may be static, adjustable in length, and or adjustable in orientation. The adjustability of the lever arm could be done manually or automatically though additional actuators. One example is a lever arm that has two configurations: one for walking, and one for running.

An exoskeleton may also include mounting points for temporary parallel actuators. For example, an ankle exoskeleton may be designed to temporarily accept a parallel damper. The parallel damper could be used for landing from a fall. The damper may be reusable or a material that is destroyed after a single use.

An exoskeleton designed with a unidirectional actuator may have more than one configurations. That configuration can be the attachment point of the transmission. One example is a belt that can be mounted on two different points. In one configuration is allows powered plantarflexion, and in the other it allows powered dorsiflexion.

The high peak to average current ratio of typical exoskeleton actuators can be problematic for batteries and for energy efficiency. Power electronics can be used, in combination with energy storage (battery, capacitor, inductor) to reduce this ration while maintaining a constant bus voltage.

In use, the motor 1 is powered and controlled by the onboard control electronics 15 and a battery (e.g. 532 of FIG. 16). Angle of the motor 1 can be measured with the motor angle sensor 16, 17 and the angle of the ankle output joint is preferably measured with a separate angle joint sensor 7, 8. The sensor can be any type of sensor, such as an optical encoder, magnetic angle sensor, hall effect sensor, potentiometer, capacitive sensor, inductive sensor, or a linear variable differential transformer (LVDT). The various sensors can be used alone or in any combination.

In one example, the motor angle sensor 16, 17 and ankle angle sensor 7, 8 are preferably related when the actuator is engaged and exerting torque, but independent when the actuator is not engaged. Thus, during operation, the control electronics 15 controls the take up and pay of the drive belt about the drive spool. The different components of the exoskeleton 30 are electronically interconnected to the control electronics 15 so they may be controlled and monitored as required. For example, the sensors, motor 1 and power supply, such as a battery (not shown), are electronically connected to the control electronics 15 whereby the timing of such take up and pay out of the drive belt 3 via the motor 1 can be timed or synchronized to the gait of the user, with the assistance of the sensors, so that the plantar flexion torque can be applied by the exoskeleton at the appropriate time to use the work created by that torque to assist in the plantar flexion of the joint to, in turn, facilitate walking.

For example, the control electronics 15 can be programmed to carry out different tasks, such as inertial sensor readings, clock synchronization between the micro-controllers, serial and PC communication, non-volatile memory interface, and the like. These features enable better high-level controllers. For example, a 168 MHz Cortex-M4F STM32F427 controller may be used to carry out computing cycles available for executing high-level algorithms concerning control of the exoskeleton 30. Field Programmable Gate Arrays (FPGA), Complex Programmable Logic Devices (CPLD), Application Specific Integrated Circuits (ASIC), and Graphical Processing Units (GPU) may also be used for hardware math acceleration and control. This makes it also possible to use machine learning techniques in real time.

In operation the exoskeletons use one or many computing elements (microprocessor, micro-controller, programmable logic) and a selection of sensors to control the various actuators or single actuator. In the instant disclosure, there can be at least two fundamental modes that the exoskeletons operates under: a zero torque mode and an active mode.

During zero torque mode the exoskeleton is programmed such that it does not apply any torque about the augmented joint or is controlled to apply as close to zero torque as possible. The present disclosure considers that there may be various levels of zero torque. If the device had zero mass and no artificial joints, then the user would truly feel zero torque since there would be no device! If the device has mass but no artificial joints or actuators, then the user would only feel the inertia of the added mass. This could be perceived as an additional torque about the joint. If the device has an artificial joint, then the user will feel a drag torque because of the physical joint. This torque results from friction in the joint and/or bearings. These torques are likely imperceivable by the user, due to their small magnitudes, just like the forces created by the upper part of a tall boot or by elastic socks or pants (ex: compression socks, leggings, etc.)

Substantial torques about the joint are felt when the device includes an actuator. For example, assume a device that has a motor directly connected to the joint. The user will experience the inertia of the motor rotor as an external torque that is proportional to the angular acceleration. Furthermore, the user will experience any friction in the motor as a resistive torque. If current is able to flow through the leads of the motor, then the user may also experience a drag torque produced by the back EMF of the motor. The motor could be controlled to attempt to maintain zero torque on the joint. This type of controller can mitigate the effects of motor drag torques, but it is exceedingly difficult to develop a controller that can anticipate the motion of the user and compensate for the inertial effects of the motors. The controller must know the current acceleration of the joint and appropriately control the motor to match the joint position, velocity and acceleration. Sensor delay, computational delay, and filtering delay all contribute to system delays that make it impossible to know the exact dynamics state of the joint and apply the appropriate control.

An actuator that is capable of disengaging from the joint can exert a true zero-torque against the joint. One example would be a motor that has a clutch between the motor and the joint. When the clutch disengages the motor from the joint, the user would not experience the torques due to the motor. However, this requires additional mechanical complexity and mass. Another option is to implement a unidirectional actuator that is only capable of applying forces in a single direction. For example, an actuator that uses a cord to exert forces across the joint can exert a torque in one direction but is unable to exert a torque in the opposite direction. Simply, a cord can only pull and not push. A simple controller can be programmed to maintain slack in the cord and ensure that no forces are being applied to the joints. Alternatively, the cord can be kept in a position that is beyond the angular range of the joint and thus can never be engaged. A cam and follower are another example of a unidirectional actuator.

A zero-torque mode can important for a number of reasons. One such reason is for observing the natural behavior of a user while wearing an exoskeleton without being impeded by forces generated by the actuators or the weight of the exoskeleton itself. During zero-torque mode, the exoskeleton can use its sensors and onboard microprocessors to measure and analyze the unimpeded motion of a user. For example, a lower limb exoskeleton can measure gait parameters of the user while walking during zero-torque control. Important bio-mechanical parameters can include joint angles, velocities and accelerations, limb accelerations and angular velocities, and the timing of these parameters with respect to periods of the gait cycle.

During an active mode, the exoskeleton can have periods of applying torque and periods of applying zero-torque. The exoskeleton controller may also continue to measure the user's gait parameters during the active mode to continuously adjust output of the actuators during use. The algorithm that determines the application of torque may use parameters measured during the zero-torque mode, the active mode, or a combination of the two.

An ankle exoskeleton, like the one disclosed herein, can use various strategies to apply torque about the ankle. The present discussion is made with respect to the ankle; however, it is understood that the present exoskeleton, controller, and program can be used with any bio-mechanical joint in the body. The exoskeleton can be configured to apply torque about the ankle as a function of the measured ankle angle. The ankle angle may be measured with an angle sensor and/or inertial measurement units. The ankle angle estimate may be adjusted as a function of the torque applied.

Alternatively, or additionally, the exoskeleton actuators can apply torque about the ankle as a function of the measured shank angle. The shank angle may be measured with various angle sensors and/or various inertial measurement units. The shank angle may be adjusted as a function of the torque applied. It is understood that the term "shank angle," as used herein, is the global angle of the shank's longitudinal axis with respect to the floor/earth or a relative change in shank angle over a period of time. In effect, the torque of the individual actuators can be changed as a function of the measured shank angle. For example, the shank angle can be set to zero upon the measurement of the heel striking the ground, then measure a change in shank angle with an integrated gyroscope located on the shank itself.

In general, the exoskeleton can additionally, or alternatively, apply torque about the ankle as a function of time. The present algorithm can also use a combination of exoskeleton torque profile strategies.

One exemplary method for measuring the shank angle of user wearing an exoskeleton is to attach a microprocessor to the exoskeleton and a gyroscope sensor to the shank of the user. The gyroscope sensor can be the only sensor on the exoskeleton, or the gyroscope can be used in combination with other sensors on the exoskeleton. The gyroscope measures the angular velocity of the shank. The control algorithm can receive the angular velocity and estimates the shank angle. The algorithm is as follows:

1) The angular velocity is measured to be above a threshold;
2) The angle is set to zero;
3) The swing time is set to zero;
4) The angle is computed as the time integral of the angular velocity;
5) The swing time is incremented;
6) The angular velocity is measured to be below the threshold;
7) The peak swing angle is set to be the current estimate of the angle;
8) The swing time is set at the current time;
9) The shank angle is set to zero;
10) The stance time is set to zero;
11) The shank angle is computed as the time integral of the angular velocity; and
12) The stance time is incremented.

The shank angle can then be transmitted to the exoskeleton controller as an input variable for a torque output function for the actuator. The algorithm can also be narratively described as follows, the angular velocity of the limb can be continuously received by the controller, typically at a fixed frequency. During each control loop, the controller can use logic to determine which state it should be in. For example, if the angular velocity is below a predetermined threshold, and the controller is not currently in the swing state, then the controller enters the swing state. The swing state can be controlled, for example if the controller was not in the swing state during the previous cycle, then 1) the swing timer is set to 0 and the swing angle is set to a value (0 in one embodiment, but it does not have to be and can be change over time); 2) increment the swing timer; 3) increase the swing angle by integrating angular velocity, 4) if the angular velocity is above a certain threshold and if the swing timer and/or swing angle are above certain thresholds, then the swing angle is saved and used by controller and the swing timer is saved and used by controller, and the controller does not re-enter the swing state in the next cycle; 5) if the previous conditions are not met, then re-enter the swing state in the next cycle.

In another, or additional, exemplary method, a user can first wear the exoskeleton and power it on. The user may use a separate device, such as a phone, tablet, or computer, to manually adjust the parameters of the exoskeleton. These parameters may include: gender; age; height; weight; carried weight; desired walking speed; desired running speed; limb lengths; type of terrain; proficiency; desired gait (jump, squat, crawl, etc.); energy harvesting mode; known gate pathologies or injuries; and other preference: e.g. speed increase vs calorie saving.

The user may also select pre-recorded profiles that describe control strategies. The device can additionally or alternatively perform a calibration routine. Calibration may include sensor zeroing, such as angle sensors and inertial measurement sensors. The calibration may also include the synchronization of an actuator motor and joint angle sensor. The calibration may include having the user do specific motions to measure his range of motion and maximum joint speeds. If the user has not selected a pre-recorded profile, then the user may perform a series of motions while the exoskeleton is in a zero-torque control condition, as discussed above. If the actuator is a unidirectional actuator, such as a winch actuator, then the zero-torque control may be achieved by unwinding the cord to a position that cannot be engaged by the ankle joint. The zero-torque control condition may also be achieved by the controlling the cord to maintain a certain level of slack by controlling the motor position as a function of the ankle position.

While the exoskeleton is in a zero-torque mode, the controller can measure various gait parameters using various sensors. The sensors may include: timers; accelerometers; gyroscopes; angle sensors; strain gages; pressure sensors; force sensors; magnetic field sensors; speed sensors; optical sensors; surface electrodes; implanted electrodes; implanted distance measurement sensors; GPS; WIFI transmitter/receiver; BLUETOOTH; cellular transmitter/receiver; near field radios; and range finders.

The parameters measured by the various sensors may include various combinations of: step time; swing time; stance time; ankle angles as a function of gait time; shank angles as a function of gait time; accelerations as a function of gait time; angular velocities; foot pressure magnitude and location as a function of gait time; muscle activation magnitude; and global position. The instant system is additionally capable of deriving certain measurements as a function of the measured parameters. For example, the derived measurements can include: measurements as a function of another measurement; ankle angle during range of shank angle; muscle activation during range of ankle angle; accelerations during period of time; peak measurements as a function of another measurement; peak ankle angle during a period of time; peak angular velocity during swing; peak pressure during a range of ankle measurements; and peak muscle activation during a period of time.

After a period of time, or number of gait events, the exoskeleton may enter an active mode. The exoskeleton can monitor the gait and can estimates user gait patterns. The exoskeleton controller may use statistical models to predict the level of confidence that a certain gait is detected. Regressions may be used to predict certain gait parameters as a function of one or many sensor measurements. For example, during the zero-torque mode, the controller may compare the peak plantarflexion ankle angle and the step time of a single step. A regression model has been developed to correlate step time with the peak plantarflexion ankle angle. This correlation would can additionally measure the strength of the correlation. If the strength is high enough, the controller could use the step time of a step to predict the peak plantar flexion angle of the next step. This strategy could be used with any combination of measured and or derived parameters.

If the exoskeleton controller does not recognize a specific gait pattern or has low confidence in the regression model, the controller may choose to enter a zero-torque mode at any time. The zero-torque mode may be entered in a gradual manner to reduce the effects of abrupt transitions. The exoskeleton controller may also choose to enter the zero-torque control mode if an error is detected such as a missing sensor, broken actuator or nearly depleted battery.

If more than one exoskeleton is worn at a time (i.e. a right and left exoskeleton) the multiple exoskeletons may communicate with each other wirelessly or over wire. The multiple exoskeletons can additionally communicate with a central controller, which can coordinate controls of both of the exoskeletons. The multiple exoskeletons can share sensory information and parameters in real time with each other and use these measured and derived parameters to inform the join control of the system as a whole. For example, the ankle angle of the left leg could be used to inform the controller of the right leg. Calculations may also be shared across multiple systems to reduce computational burden. The two individual devices can do their share of the same calculation, or they can use different algorithms. The algorithm with the highest confidence rating can then be used to control the combination of the two devices. The two devices can additionally, or alternatively, run the exact same algorithm as a form of redundancy.

In some embodiments, loop optimizations can be performed to optimize the performance of the instant exoskeleton, or other exoskeletons. The control algorithm can apply slight perturbations to the system (change power level, add delay or anticipate action, change gains, etc.) and use onboard and off-board sensors to measure the impact on the user. One example is a master algorithm that tries to minimize the user's heart rate frequency at a given energy. User feedback, obtained via an application or by pressing on a button, can be used as part of the optimization strategy.

The exoskeleton can be part of a wired or wireless network of device. These devices can include the one or more of following: a mobile device (e.g., a phone, a tablet, etc.); Other exoskeleton controllers; a computer or a laptop; a cellular network; wireless/wired sensors; heart rate monitors; temperature sensors; oxygen consumption sensors; muscle activation sensors; lab equipment; and gym devices (treadmill, stair climber, elliptical machine, etc.).

The exoskeleton control systems can receive updates over a network. For example, a mobile device may be able to send an update to the exoskeleton to inform the controller. The exoskeleton data may be uploaded to a central database, where multiple user data is collected, combined and analyzed. The exoskeleton data may also be stored on a decentralized network. These data may be used to inform generic controllers. A mobile device may also be able to provide information to the user about the state of the exoskeleton, such as: battery level; missing or broken sensors; broken actuators; missing communications; errors; power/energy/torque provided to the user; number of steps; energy saved; distance traveled; map of travel; fitness metrics; and total time use and other usage statistics.

The described exoskeleton can be worn on one leg or on both legs in a bilateral configuration. When the exoskeleton is worn in a bilateral configuration, the two exoskeletons can communicate with wires or wireless communication protocols to share state information for purposes of control and telemetry.

It would be appreciated by those skilled in the art that various changes and modifications can be made to the illustrated embodiments without departing from the spirit of the present invention. All such modifications and changes are intended to be covered by the appended claims.

What is claimed is:

1. A control system for biomechanical exoskeleton joint for generating torque about an axis of rotation of a body joint, comprising:

at least one exoskeleton member configured to be arranged on a limb of a user;
a first control device connected to the at least one exoskeleton member;
a first actuator configured to be mechanically connected to the limb of the user; and
at least one sensor configured and arranged to sense an angle of the limb relative to the ground;
wherein the first control device is configured and arranged to use the angle to control the at least one exoskeleton member, and
wherein the first control device is further configured and arranged to,
determine if the at least one exoskeleton member was in the swing state during the previous cycle, if not
then a swing timer is set to 0 and a swing angle is set to a value,
increment the swing timer,
increase the swing angle by integrating angular velocity,
if an angular velocity of the at least one body segment is above a predetermined threshold and if the swing timer and/or swing angle are above predetermined thresholds, then the swing angle and swing timer are saved and used by the first control device, and
the first control device does not re-enter the swing state in the next cycle;
if the at least one exoskeleton member was in the swing state during the previous cycle, then re-enter the swing state in a next cycle.

2. The control system of claim 1, wherein the at least one sensor is a gyroscope sensor.

3. The control system of claim 1, further comprising,
at least two exoskeleton members configured to be arranged on respective limbs of the user;
wherein the first control device is configured and arranged to use the angle to control the at least two exoskeleton members.

4. The control system of claim 3, wherein the at least two exoskeleton devices communicate wirelessly.

5. The control system of claim 1, wherein the angle is a shank angle.

6. The control system of claim 1, wherein data of the at least one control device is configured and arranged to be read or written from a computer server or cloud server.

7. The control system of claim 1, wherein the first control device is configured and arranged to change an output torque of the first actuator as a function of a measured body segment angle.

8. The control system of claim 7,
wherein the limb of the user is a lower leg, and
wherein the angle is the shank angle.

9. The control system of claim 7,
wherein the output torque of the at least one first actuator increases as the body segment angle increases.

10. The control system of claim 1, wherein the first control device is configured and arranged to calculate a phase of gait of the user as a function of the body segment angle.

* * * * *